US007838223B2

(12) United States Patent
Rivkees et al.

(10) Patent No.: US 7,838,223 B2
(45) Date of Patent: Nov. 23, 2010

(54) DNA DIAGNOSTIC SCREENING FOR TURNER SYNDROME AND SEX CHROMOSOME DISORDERS

(75) Inventors: Scott Rivkees, Orange, CT (US); Jeffrey Gruen, Hamden, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 11/402,775

(22) Filed: Apr. 12, 2006

(65) Prior Publication Data

US 2006/0292602 A1 Dec. 28, 2006

Related U.S. Application Data

(60) Provisional application No. 60/671,214, filed on Apr. 13, 2005.

(51) Int. Cl.
C12Q 1/68 (2006.01)
C07H 21/04 (2006.01)
C12P 19/34 (2006.01)
(52) U.S. Cl. .......................... 435/6; 536/24.3; 435/91.2
(58) Field of Classification Search ........................ None
See application file for complete search history.

(56) References Cited

U.S. PATENT DOCUMENTS

| 6,258,568 B1 | 7/2001 | Nyren | |
|---|---|---|---|
| 2003/0092019 A1* | 5/2003 | Meyer et al. ................... | 435/6 |

OTHER PUBLICATIONS

Home reference (ghr.nlm.nih.gov/chromosome=X).*
Meng et al (The Journal of Endocrinology & Metabolism (2005) vol. 90, pp. 3419-3422, published online Mar. 29, 2005).*
Donaghue et al ( Prenatal Diagnosis (2003) pp. 201-210).*
Hirschhorn et al. (Genetics in Medicine. vol. 4, No. 2, pp. 45-61, Mar. 2002).*
Alderborn et al., "Determination of Single-Nucleotide Polymorphisms by Real-Time Pyrophosphate DNA Sequencing," *Methods*, vol. 12, pp. 1249-1258, 2000.
Blaschke, et al., "SHOX: Growth, Leri-Weill and Turner Syndromes," *Trends Endocrinol. Metab.*, vol. 11(6): pp. 227-230, 2000.
Boucher, et al., "Breakpoint Analysis of Turner Patients with Partial Xp Deletions: Implications for the Lymphoedema Gene Location,"*J. Med. Genet.*, vol. 38, pp. 591-598, 2001.
Canto, et al., "Gonadoblastoma in Turner Syndrome Patients with Nonmosaic 45,X Karyotype and Y Chromosome Sequences," *Cancer Genetics and Cytogenetics*, vol. 150, pp. 70-72, 2004.
Chen et al., "Comparison of GenFlex Tag Array and Pyrosequencing in SNP Genotyping,"*Journal of Molecular Diagnostics*, vol. 5(4), pp. 243-249, 2003.
Cirigliano, et al., "Rapid Detection of Chromosomes X and Y Aneuploidies by Quantitative Fluorescent PCR," *Prenatal Diagnosis*, vol. 19, pp. 1099-1103, 1999.
Cormier-Daire, et al., "SHOX Gene Mutations and Deletions in Dyschondrosteosis or Leri-Weill Syndrome," *Acta Paediatr. Suppl.*, vol. 88, pp. 55-59, 1999.

Elahi, et al., "Pyrosequencing: A Tool for DNA Sequencing Analysis," *Methods in Molecular Biology*, vol. 255, pp. 211-220, 2004.
Fakhrai-Rad, "Pyrosequencing: An Accurate Detection Platform for Single Nucleotide Polymorphisms," *Human Mutatation*, vol. 19, pp. 479-485, 2002.
Gravholt, "Epidemiological, Endocrine and Metabolic Features in Turner Syndrome," *European Journal of Endocrinology*, vol. 151, pp. 657-687, 2004.
Gunther, et al., "Ascertainment Bias in Turner Syndrome: New Insights From Girls Who Were Diagnosed Incidentally in Prenatal Life," *Pediatrics*, vol. 114(3), pp. 640-644, 2004.
Haberecht, et al., "Functional Neuroanatomy of Visual-Spatial Working Memory in Turner Syndrome,"*Brain Mapping*, vol. 14, pp. 96-107, 2001.
Hall, et al., "Turner Syndrome and its Variants," *Pediatric Clinics of North America*, vol. 37(6), pp. 1421-1440, 1990.
Heinrichs, et al., "Blood Spot Follicle-Stimulating Hormone During Early Postnatal Life in Normal Girls and Turner's Syndrome," *Journal of Clinical Endocrinology and Metabolism*, vol. 78(4), pp. 978-981, 1994.
Henn, et al., "Mosaicism in Turner's Syndrome," *Nature*, vol. 390, p. 569, 1997.
Hull, et al., "Growth Hormone Therapy and Quality of Life: Possibilities, Pitfalls and Mechanisms," *Journal of Endocrinology*, vol. 179, pp. 311-333, 2003.
Kleczkowska, et al., "Cytogenetic Findings in a Consecutive Series of 478 Patients with Turner Syndrome. The Leuven Experience 1965-1989," *Genet. Couns.*, vol. 1(3-4), pp. 227-233, 1990.
Kosho, et al., "Skeletal Features and Growth Patterns in 14 Patients with Haploinsufficiency of SHOX: Implications for the Development of Turner Syndrome,"*J. Clin. Endocrinol. Metab.*, vol. 84(12). pp. 4613-4621, 1999.
Longui, et al., "Molecular Detection of XO—Turner's Syndrome," *Genetics and Molecular* Research, vol. 1, pp. 266-270, 2002.
Massa, et al., "Trends in Age at Diagnosis of Turner Syndrome" *Arch. Dis. Child.*, vol. 90, pp. 267-268, 2005.
Meng et al., ":Detection of Turner Syndrome Using High-Throughput Quantitative Genotyping," *The Journal of Clinical Endocrinology & Metabolism*, vol. 90(6), pp. 3419-3422, 2005.
Parker, et al., "Screening Girls with Turner Syndrome: The National Cooperative Growth Study Experience," *Journal of Pediatrics*, vol. 143, pp. 133-135, 203.
Plotnick, et al., "Growth Hormone Treatment of Girls with Turner Syndrome: The National Cooperative Growth Study Experience," *Pediatrics*, vol. 102, pp. 479-481, 1998.
Pourmand, et al., "Multiplex Pyrosequencing," *Nucleic Acids Res.*, vol. 30(7), pp. e31, 2002.
Ranke, et al., "Turner's Syndrome," *Lancet*, vol. 358, pp. 309-314, 2001.

(Continued)

*Primary Examiner*—Steven C Pohnert
(74) *Attorney, Agent, or Firm*—Drinker Biddle & Reath LLP

(57) ABSTRACT

The present invention encompasses methods, assays and kits for the diagnosis, screening and identification of Turner syndrome and other disorders of sexual differentiation in a human using single nucleotide polymorphisms present on the X and Y chromosomes.

3 Claims, 9 Drawing Sheets

OTHER PUBLICATIONS

Rosenfeld, et al., "Growth Hormone Therapy of Turner's Syndrome: Beneficial Effect on Adult Height," *The Journal of. Pediatrics.*, vol. 132, pp. 319-324, 1998.

Ross, et al., "Developmental Changes in Motor Function in Girls with Turner Syndrome," *Pediatric Neurology*, vol. 15, pp. 317-322, 1996.

Ross, et al., "Effects of Estrogen on Nonverbal Processing Speed and Motor Function in Girls with turner's Syndrome," *Journal of Clinical Endocrinology and Metabolism*, vol. 83, pp. 3198-3204, 1998.

Ross et al., "Androgen-Responsive Aspects of Cognition in Girls with Turner Syndrome," *The Journal of Clinical Endocrinology & Metabolism*, vol. 88(1), pp. 292-296, 2003.

Saenger, et al., "Recommendations for the Diagnosis and Management of Turner Syndrome," *The Journal of Clinical Endocrinology & Metabolism*, vol. 86(7), pp. 3061-3069, 2001.

Savendahl, et al., "Delayed Diagnoses of Turner's Syndrome: Proposed Guidelines for Change," *The Journal of Pediatrics*, vol. 137, pp. 455-459, 2000.

Tsezou, et al., "Molecular Genetics of turner Syndrome: Correlation with Clinical Phenotype and Response to Growth Hormone Therapy," *Clinical Genetics*, vol. 56, pp. 441-446, 1999.

Uehara, et al., "X Chromosome Inactivation Patterns in 45,X/46,XX Mosaics," *Journal of Human Genetics*, vol. 46, pp. 126-131, 2001.

Vlasak, et al., "Screening of Patients with Turner Syndrome for 'Hidden' Y-Mosaicism," *Klin. Padiatr.*, vol. 211(1), pp. 30-34, 1999.

\* cited by examiner

FIG. 3

| Chromosome band: | Xp22.22 | Xp11.4 | Xq13.1 | Xq13.2 | Xq21.2 | Xq22.1 | Xq26.2 | Xq26.3 | Xq27.2 | Xq28 |
|---|---|---|---|---|---|---|---|---|---|---|
| Marker: | 2 | 5 | 8 | 9 | 11 | 14 | 18 | 19 | 20 | 22 |
| SNP: | C/T | C/T | C/T | C/T | C/T | G/C | C/T | C/T | C/T | C/T |
| Karyotype | %T | %T | %T | %T | %T | %G | %T | %T | %T | %T |
| 45,X | 100 | 0 | 100 | 0 | 100 | 100 | 0 | 0 | 0 | 0 |
| 45,X | 0 | 100 | 100 | 100 | 100 | 0 | 100 | 0 | 0 | 100 |
| 45,X | 100 | 0 | 100 | 0 | 100 | 0 | 0 | 100 | 0 | 100 |
| 45,X/46,X,del(X)(pter>q11:) | 0 | 100 | 47 | 100 | 43.4 | 60.9 | 0 | 60.3 | 0 | 0 |
| 45,X/46,X,del(X)(qter>cen:)/46,X,I(X)(qter>cen>qter) | 88.6 | 100 | 100 | 100 | 20.9 | 28.9 | 19.9 | 100 | 0 | 0 |
| 45,X/46,X,del(Y)(pter>q11.2:) | 100 | 0 | 100 | 100 | 0 | 100 | 100 | 100 | 100 | 39.6 |
| 45,X/46,X,del(Y)(qter>p11.2:) | 100 | 0 | 40.1 | 0 | 38.9 | 61.3 | 33.3 | 100 | 100 | 0 |
| 45,X/46,X,dic(X)(qter>p11::p11>qter) | 100 | 0 | 100 | 54.7 | 71.8 | 51.9 | 76.4 | 72.4 | 100 | 36.8 |
| 45,X/46,X,I(X)(qter>cen>qter) | 0 | 100 | 100 | 0 | 66.6 | 100 | 66 | 0 | 0 | 0 |
| 45,X,+frag/46,X,I(Y)(qter>cen>qter) | 100 | 0 | 100 | 100 | 0 | 100 | 100 | 0 | 0 | 0 |
| 46,X,add(X).ish del dup(X)(wcpX+,cdy16c07-).rev ish d | 45.2 | 100 | 48.1 | 54.7 | 0 | 53.9 | 0 | 64.1 | 100 | 0 |
| 46,X,add(X).ish del dup(X)(wcpX+,cdy16c07-).rev ish d | 0 | 0 | 100 | 0 | 0 | 100 | 100 | 0 | 100 | 0 |
| 46,X,dic(X)(qter>p11::p11>qter),inv(2)(pter>p11::q13>p) | 0 | 100 | 65.8 | 66.8 | 100 | 63.6 | 100 | 63.5 | 63.7 | 38.5 |
| 46,X,I(X)(qter>cen>qter) | 0 | 0 | 100 | 100 | 69.7 | 100 | 71.3 | 100 | 0 | 0 |
| 46,X,I(X)(qter>cen>qter) | 100 | 100 | 100 | 100 | 66.6 | 39 | 37.1 | 66.7 | 0 | 100 |
| 47,XXX | 35.8 | 33.6 | 66.8 | 0 | 100 | 63.7 | 100 | 100 | 0 | 67 |
| 47,XXX | 34.8 | 64 | 64.4 | 100 | 65.3 | 63.7 | 34.4 | 100 | 66.4 | 65.8 |
| 47,XXY | 49.3 | 100 | 100 | 100 | 49.1 | 53.8 | 50.4 | 0 | 0 | 48.4 |
| 47,XXY | 50.1 | 51 | 53.9 | 100 | 49.4 | 49.4 | 100 | 47.6 | 0 | 50.8 |
| 47,XXY | 100 | 100 | 10 | 100 | 100 | 100 | 0 | 100 | 0 | 100 |
| 47,XYY | 0 | 0 | 100 | 100 | 0 | 100 | 0 | 100 | 100 | 0 |
| 47,XYY | 100 | 0 | 100 | 100 | 0 | 100 | 0 | 90.8 | 0 | 0 |
| 48,XXYY | 48.6 | 50 | 100 | 49.9 | 0 | 53.3 | 46.3 | 46.6 | 49.2 | 100 |
| 48,XXYY | 0 | 48.6 | 100 | 52.2 | 100 | 100 | 51.4 | 46.9 | 100 | 49.1 |
| 49,XXXXY | 53.7 | 49.3 | 100 | 100 | 48.7 | 0 | 100 | 0 | 53 | 53 |
| 49,XYYYY | 100 | 0 | 100 | 100 | 0 | 100 | 100 | 100 | 0 | 100 |
| CEPH1331, 46, XX | 0 | 0 | 53 | 53.6 | 0 | 100 | 47.8 | 100 | 0 | 0 |
| CEPH1331, 46, XX | 47.3 | 50.5 | 51.5 | 50.6 | 51.8 | 49.6 | 100 | 51 | 52.2 | 53.1 |
| CEPH1331, 46, XX | 53 | 49.8 | 100 | 100 | 51.6 | 50.9 | 51.4 | 49 | 0 | 0 |
| CEPH1331, 46, XX | 0 | 0 | 100 | 52.4 | 0 | 100 | 52.6 | 50.1 | 53.7 | 48.9 |
| CEPH1331, 46, XX | 0 | 0 | 100 | 100 | 54.1 | 100 | 49.3 | 47.8 | 52.2 | 52.9 |
| CEPH1331, 46, XX | 47.9 | 50 | 50.7 | 0 | 50.1 | 50.5 | 50 | 49.2 | 52.5 | 53.4 |
| CEPH1331, 46, XX | 48.5 | 47.8 | 55 | 49.5 | 100 | 54.9 | 46.4 | 0 | 0 | 0 |
| CEPH1331, 46, XX | 53.2 | 53 | 100 | 53.6 | 0 | 100 | 0 | 51.3 | 51.9 | 0 |
| CEPH1331, 46, XY | 56 | 50.9 | 100 | 100 | 46.1 | 48 | 49.6 | 49.3 | 49.9 | 53 |
| CEPH1331, 46, XY | 0 | 0 | 100 | 100 | 100 | 0 | 100 | 100 | 100 | 0 |
| CEPH1331, 46, XY | 100 | 0 | 100 | 100 | 0 | 100 | 100 | 0 | 0 | 100 |
| CEPH1331, 46, XY | 0 | 0 | 100 | 100 | 0 | 0 | 100 | 49 | 0 | 100 |
| CEPH1331, 46, XY | 0 | 0 | 100 | 100 | 100 | 0 | 0 | 0 | 0 | 100 |
| CEPH1331, 46, XY | 100 | 0 | 100 | 100 | 0 | 100 | 100 | 100 | 0 | 0 |
| CEPH1331, 46, XY | 0 | 0 | 100 | 100 | 0 | 100 | 0 | 0 | 0 | 0 |
| CEPH1331, 46, XY | 0 | 0 | 100 | 100 | 0 | 0 | 0 | 0 | 0 | 0 |
| CEPH1375, 46, XY | 100 | 0 | 100 | 100 | 0 | 0 | 100 | 100 | 0 | 0 |
| CEPH1375, 46, XY | 100 | 0 | 0 | 100 | 0 | 0 | 0 | 0 | 100 | 0 |
| CEPH1420, 46, XY | 0 | 0 | | 100 | 0 | 100 | 100 | 100 | 100 | 100 |

FIG. 5

| | 2 | 5 | 8 | 9 | 11 | 14 | 18 | 19 | 20 | 22 | | |
|---|---|---|---|---|---|---|---|---|---|---|---|---|
| Panel | %T | %T | %T | %T | %T | %G | %T | %T | %T | %T | Hetero | |
| | Allele | Allele | Allele | Allele | Allele | Allele | Allele | Allele | Allele | Allele | Marker | Karyo |
| HD01 | 46.0 | 47.6 | 0.0 | 100 | 0.0 | 53.1 | 100.0 | 49.8 | 51.6 | 0.0 | 5 | XX |
| Northern | 51.5 | 49.0 | 100.0 | 53.6 | 50.5 | 100.0 | 100.0 | 100.0 | 0.0 | 0.0 | 4 | XX |
| European | 0.0 | 0.0 | 100.0 | 100.0 | 100.0 | 100.0 | 0.0 | 0.0 | 100.0 | 0.0 | 0 | XY |
| | 100.0 | 51.0 | 50.5 | 52.9 | 0.0 | 100.0 | 100.0 | 53.1 | 51.0 | 52.8 | 6 | XX |
| | 100.0 | 100.0 | 50.0 | 100.0 | 100.0 | 100.0 | 100.0 | 0.0 | 0.0 | 100.0 | 1 | XX |
| | 100.0 | 100.0 | 100.0 | 100.0 | 0.0 | 100.0 | 51.4 | 52.6 | 0.0 | 0.0 | 2 | XX |
| | 0.0 | 0.0 | 100.0 | 0.0 | 0.0 | 100.0 | 100.0 | 0.0 | 0.0 | 100.0 | 0 | XY |
| | 0.0 | 0.0 | 100.0 | 0.0 | 100.0 | 100.0 | 100.0 | 0.0 | 0.0 | 0.0 | 0 | XY |
| | 0.0 | 100.0 | 47.7 | 100.0 | 100.0 | 100.0 | 50.8 | 100.0 | 51.1 | 46.1 | 4 | XX |
| | 0.0 | 100.0 | 0.0 | 100.0 | 0.0 | 100.0 | 0.0 | 0.0 | 100.0 | 0.0 | 0 | XY |
| HD32 | 0.0 | 0.0 | 100.0 | 0.0 | 0.0 | 100.0 | 0.0 | 100.0 | 0.0 | 100.0 | 0 | XY |
| Chinese | 0.0 | 48.3 | 100.0 | 0.0 | 52.8 | 100.0 | 100.0 | 100.0 | 0.0 | 100.0 | 2 | XX |
| | 0.0 | 100.0 | 100.0 | 0.0 | 0.0 | 100.0 | 100.0 | 100.0 | 0.0 | 100.0 | 0 | XY |
| | 0.0 | 100.0 | 100.0 | 0.0 | 0.0 | 100.0 | 100.0 | 100.0 | 0.0 | 100.0 | 0 | XY |
| | 0.0 | 100.0 | 100.0 | 0.0 | 100.0 | 100.0 | 0.0 | 100.0 | 100.0 | | 0 | XY |
| | 100.0 | 0.0* | 100.0 | 0.0 | 0.0 | 100.0 | 0.0 | 0.0 | 0.0 | 0.0 | 0 | XY |
| | 100.0 | 100.0 | 100.0 | 0.0 | 0.0 | 0.0 | 100.0 | 0.0 | 100.0 | 0.0 | 0 | XY |
| | 100.0 | 48.2 | 100.0 | 0.0 | 0.0 | 100.0 | 46.2 | 55.5 | 52.9 | 100.0 | 4 | XX |
| | 100.0 | 0.0 | 100.0 | 0.0 | 47.4 | 46.5 | 100.0 | 100.0 | 47.6 | 100.0 | 3 | XX |
| | 100.0 | 100.0 | 100.0 | 0.0 | 0.0 | 0.0 | 100.0 | 100.0 | 0.0 | 100.0 | 0 | XY |
| HD04 | 45.5 | 100.0 | 100.0 | 47.6 | 0.0 | 100.0 | 49.9 | 100.0 | 46.6 | 55.6 | 5 | XX |
| African | 52.0 | 100.0 | 54.7 | 100.0 | 0.0 | 52.0 | 48.9 | 100.0 | 100.0 | 49.2 | 5 | XX |
| American | 11.7 | 100.0 | 49.9 | 0.0 | 0.0 | 100.0 | 50.9 | 51.9 | 90.1 | 0.0 | 3 | XX |
| | 0.0 | 100.0 | 100.0 | 52.8 | 59.2 | 100.0 | 0.0 | 0.0 | 50.8 | 0.0 | 3 | XX |
| | 0.0 | 0.0 | 100.0 | 0.0 | 51.4 | 48.9 | 0.0 | 100.0 | 100.0 | 55.7 | 3 | XX |
| | 50.0 | 100.0 | 49.9 | 49.2 | 0.0 | 100.0 | 0.0 | 100.0 | 100.0 | 52.2 | 4 | XX |
| | 0.0 | 100.0 | 100.0 | 100.0 | 0.0 | 0.0 | 100.0 | 100.0 | 100.0 | 11.0 | 0 | XY |
| | 49.9 | 100.0 | 100.0 | 100.0 | 49.0 | 51.5 | 0.0 | 0.0 | 55.3 | 51.0 | 5 | XX |
| | 100.0 | 100.0 | 0.0* | 100.0 | 0.0 | 53.1 | 0.0 | 55.8 | 100.0 | 54.6 | 3 | XX |
| | 100.0 | 47.6 | 50.6 | 100.0 | 0.0 | 0.0 | 0.0 | 51.9 | 51.2 | 54.8 | 5 | XX |
| HD09 | 0.0 | 100.0 | 0.0 | 100.0 | 100.0 | 0.0 | 51.1 | 50.1 | 47.1 | 0.0 | 3 | XX |
| Puerto | 100.0 | 100.0 | 100.0 | 47.4 | 100.0 | 0.0 | 49.2 | 49.7 | 0.0 | 46.6 | 4 | XX |
| Rican | 0.0 | 100.0 | 100.0 | 0.0 | 100.0 | 54.4 | 100.0 | 0.0 | 0.0 | 100.0 | 1 | XX |
| | 0.0 | 100.0 | 100.0 | 100.0 | 49.2 | 55.4 | 48.1 | 100.0 | 49.3 | 46.0 | 5 | XX |
| | 100.0 | 100.0 | 100.0 | 100.0 | 100.0 | 100.0 | 0.0 | 100.0 | 0.0 | 0.0 | 0 | XY |
| | 52.0 | 52.2 | 100.0 | 0.0 | 0.0 | 100.0 | 0.0 | 51.6 | 0.0 | 49.5 | 4 | XX |
| | 0.0 | 0.0 | 100.0 | 100.0 | 100.0 | 0.0 | 100.0 | 0.0 | 0.0 | 100.0 | 0 | XY |
| | 0.0 | 0.0 | 100.0 | 100.0 | 0.0 | 100.0 | 100.0 | 100.0 | 100.0 | 100.0 | 0 | XY |
| | 0.0 | 100.0 | 50.4 | 55.2 | 0.0 | 51.8 | 46.9 | 100.0 | 50.2 | 0.0 | 5 | XX |
| | 51.9 | 100.0 | 49.8 | 51.0 | 50.0 | 54.3 | 100.0 | 51.8 | 0.0 | 49.5 | 7 | XX |
| HD14 | 0.0 | 100.0 | 100.0 | 0.0 | 0.0 | 100.0 | 11.6 | 0.0 | 0.0 | 0.0 | 0 | XY |
| Caribbean | 51.4 | 46.7 | 51.3 | 100.0 | 100.0 | 100.0 | 52.5 | 51.9 | 49.5 | 50.1 | 7 | XX |
| | 50.5 | 100.0 | 48.7 | 55.3 | 49.2 | 51.9 | 100.0 | 100.0 | 48.8 | 47.4 | 7 | XX |
| | 49.1 | 0.0 | 100.0 | 50.0 | 50.6 | 100.0 | 55.7 | 49.8 | 0.0 | 53.1 | 5 | XX |
| | 100.0 | 100.0 | 0.0 | 100.0 | 100.0 | 100.0 | 0.0 | 0.0 | 0.0 | 100.0 | 0 | XY |
| | 100.0 | 100.0 | 48.6 | 0.0 | 0.0 | 100.0 | 49.4 | 0.0 | 49.3 | 0.0 | 3 | XX |
| | 0.0 | 0.0 | 0.0 | 100.0 | 100.0 | 100.0 | 100.0 | 100.0 | 100.0 | 100.0 | 0 | XY |
| | 100.0 | 53.6 | 100.0 | 100.0 | 0.0 | 52.2 | 53.7 | 100.0 | 54.2 | 100.0 | 5 | XX |
| | 100.0 | 0.0 | 100.0 | 0.0 | 0.0 | 100.0 | 0.0 | 100.0 | 0.0 | 0.0 | 0 | XY |
| | 50.6 | 100.0 | 100.0 | 47.9 | 100.0 | 52.5 | 50.4 | 0.0 | 0.0 | 0.0 | 4 | XX |

DNA DIAGNOSTIC SCREENING FOR TURNER SYNDROME AND SEX CHROMOSOME DISORDERS

CROSS-REFERENCE TO RELATED APPLICATIONS

The present application claims priority pursuant to 35 U.S.C. §119(e) to U.S. Provisional Application No. 60/671,214, filed Apr. 13, 2005, which is hereby incorporated by reference in its entirety herein.

STATEMENT REGARDING FEDERALLY SPONSORED RESEARCH OR DEVELOPMENT

This invention was supported in part by US Government funds (National Institutes of Health grant No. R01NS033539), and the US Government therefore has certain rights in the invention.

BACKGROUND OF THE INVENTION

Turner syndrome is the most common genetic condition affecting women (Saenger, 1997, Curr. Ther. Endocrinol. Metab. 6: 239-243; Gravholt, 2004, Eur. J. Endocrinol. 151: 657-687; Ranke and Saenger, 2001, Lancet 358: 309-314). The incidence of Turner syndrome is 1 in 1,500 to 2,000 live female births (Saenger, 1997, Curr. Ther. Endocrinol. Metab. 6: 239-243; Gravholt, 2004, Eur. J. Endocrinol. 151: 657-687; Ranke and Saenger, 2001, Lancet 358: 309-314), and occurs when an entire, or a portion of an X chromosome is deleted (Saenger, 1997, Curr. Ther. Endocrinol. Metab. 6: 239-243; Ranke and Saenger, 2001, Lancet 358: 309-314). Phenotypic features include primary hypogonadism, renal abnormalities, difficulties with spatial perception, and structural cardiac problems (Saenger, 1997, Curr. Ther. Endocrinol. Metab. 6: 239-243; Ranke and Saenger, 2001, Lancet 358: 309-314). Girls with Turner syndrome are short and have an average adult height of 4 feet 6 inches tall (Ranke and Saenger, 2001, Lancet 358: 309-314; Saenger, 2000, Endocrine, 12: 183-187; Rosenfeld, et al., 1998, J. Pediatr. 132: 319-324). Neurological manifestations include problems with spatial perception and communication skills (Bordeleau, et al., 1998, J. Emerg. Med., 16: 593-596; Johnson, et al., 1993, Neurology 43: 801-808; Money, 1993, Soc. Biol., 40: 147-151; Haberecht, et al., 2001, Hum. Brain Mapp., 14: 96-107; Pennington, et al., 1985, Cortex 21: 391-404; Ross, et al., 1996, Pediatr. Neurol., 15: 317-322; Temple and Carney, 1993, Dev. Med. Child Neurol., 35: 691-698; Ross, et al., 1998, J. Clin. Endocrinol. Metab., 83: 3198-31204). Cardiac problems include coarctation of the aorta, single coronary vessels, bicuspid aortic valves, atrial and ventricular spatial defects, and abnormalities of great vessels. Renal problems include duplex, solitary, or horseshoe kidneys. Hearing problems may be secondary to a higher frequency of otitis media or sensorineural hearing loss.

Girls with Turner syndrome generally have normal intelligence. Yet, some girls may have problems with spatial perception and mathematical skills. Thus, a modified educational curriculum may be needed. Some girls with Turner syndrome have communication problems and social difficulties. This has been found to be related to whether the X-chromosome came from the mother or the father.

Of considerable importance, girls with Turner syndrome have an average adult height of 4 feet 6 inches, which is 10 inches below the average female adult height. Recent data suggest that the short stature may be related to mutations or deletions of the SHOX gene (encoded on the X-chromosome) in Turner syndrome (Blaschke and Rappold, 2000, Trends Endocrinol. Metab., 11: 227-230; Cormier-Daire, et al., 1999, Acta Paediatr. Suppl., 88: 55-59; Boucher, et al., 2001, J. Med. Genet., 38: 59159-8; Kosho, et al., 1999, J. Clin. Endocrinol. Metab. 84: 4613-4621). Short stature in Turner syndrome has been shown to result in significant long-term problems with self-esteem. Yet, with timely initiation of growth hormone therapy, acceptable adult stature can be achieved (Rosenfeld, et al., 1998, J. Pediatr. 132: 319-324; Hull and Harvey, 2003, J. Endocrinol. 179: 311-333).

Currently, many girls with Turner syndrome are diagnosed after 10 years of age (Parker, et al., 2003, J. Pediatr., 143: 133-135; Massa, et al., 2005, Arch. Dis. Child. 90: 267-268), and recognition of associated problems may be delayed (Savendahl and Davenport, 2000, J. Pediatr., 137: 455-459). Final height may be compromised by delayed adjunctive therapy with growth hormone (Savendahl and Davenport, 2000, J. Pediatr., 137: 455-459). With later recognition, however, replacement therapy with estrogen and progestin is delayed resulting in late pubertal development (Savendahl and Davenport, 2000, J. Pediatr., 137: 455-459; Bertelloni, et al., 2003, J. Pediatr. Endocrinol. Metab., 16 Suppl 2: 307-315).

Girls with Turner syndrome are at risk for gonadal tumor development if Y chromosomal material is present (Canto, et al., 2004, Cancer Genet. Cytogenet. 150: 70-72; Vlasak, et al., 1999, Klin. Padiatr., 211: 30-34). The failure to detect small fragments of Y chromosomal material by standard karyotype analysis (Longui, et al., 2002, Genet. Mol. Res., 1: 266-270) precludes recognition of girls with Turner syndrome with potential tumor risk.

Turner syndrome represents a constellation of features that occurs when an X-chromosome is either completely deleted (45x), or when portions of the X-chromosome are deleted (Hall and Gilchrist, 1990, Pediatr. Clin. North Am., 37: 1421-1440; Uehara, et al., 2001, J. Hum. Genet., 46: 126-131; Henn and Zang, 1997, Nature, 390: 569; Kleczkowska, et al., 1990, Genet. Couns., 1: 227-233; Lippe and Saenger, 2002, In: Sperling Mass., ed. Pediatric Endocrinology. Philadelphia: Saunders, 519-564). More than half of girls with Turner syndrome have a 45X genotype. In the remaining girls there is mosaicism with two populations of cells: a proportion of cells with the normal compliment of genes (46,XX), and a proportion of cells with an X-chromosome deletion (partial or complete) (Hall and Gilchrist, 1990, Pediatr. Clin. North Am., 37: 1421-1440; Uehara, et al., 2001, J. Hum. Genet., 46: 126-131; Henn and Zang, 1997, Nature, 390: 569; Kleczkowska, et al., 1990, Genet. Couns., 1: 227-233; Lippe and Saenger, 2002, In: Sperling Mass., ed. Pediatric Endocrinology. Philadelphia: Saunders, 519-564). Other complex rearrangement (e.g. ring abnormality of the X-chromosome) causing an imbalance in the normal complement of genes encoded on the X-chromosome, can also result in Turner syndrome (Hall and Gilchrist, 1990, Pediatr. Clin. North Am., 37: 1421-1440; Uehara, et al., 2001, J. Hum. Genet., 46: 126-131; Henn and Zang, 1997, Nature, 390: 569; Kleczkowska, et al., 1990, Genet. Couns., 1: 227-233; Lippe and Saenger, 2002, In: Sperling Mass., ed. Pediatric Endocrinology. Philadelphia: Saunders, 519-564).

Disorders of sexual differentiation (DSDs) also involve sex chromosome abnormalities and/or the need to determine the identification and number of sex chromosomes. These disorders include 46XY individuals with abnormal male gonadal or genital development, 46XX individuals with abnormal female gonadal or genital development, individuals with both testes and ovaries, and individuals with extra X and/or Y chromosomes, such as those with Klinefelter syndrome.

The gold standard for diagnosis of X chromosome anueploidies and DSDs remains cytogenetic analysis (karyotype) (Longui, et al., 2002, Genet. Mol. Res., 1: 266-270). While cytogenetic analysis by light microscopy has drastically advanced in resolution over the past 50 years, it remains a labor intensive and expensive method that is not practical for population screening. Testing of blood spot follicle-stimulating hormone (FSH) during early postnatal life has been tested in girls with Turner syndrome (Heinrichs, et al., 1994, J. Clin. Endocrinol. Metab. 78: 978-981). However, perinatal changes in FSH secretion are similar to those in normal girls, thus FSH measurement are not effective for neonatal screening of Turner syndrome (Heinrichs, et al., 1994, J. Clin. Endocrinol. Metab. 78: 978-981).

Over the past decade, genotyping techniques have become faster and less expensive. A quantitative method of genotyping based on the detection of single nucleotide polymorphisms (SNPs), may prove to be advantageous in identifying chromosome deletions or additions. Single nucleotide polymorphisms (SNPs) occur about every 100 nucleotide bases (Ronaghi, 2003, Methods Mol. Biol. 212: 189-195; Elahi and Ronaghi, 2004, Methods Mol. Biol. 255: 211-220). There are thousands of SNPs available to interrogate the full length, or any specific segment, of the X and Y chromosomes (Ronaghi, 2003, Methods Mol. Biol. 212: 189-195; Elahi and Ronaghi, 2004, Methods Mol. Biol. 255: 211-220). Pyrosequencing is especially advantageous for detecting SNPs due to a high degree of quantitative accuracy, ease-of-use, and high throughput capability (Ronaghi, 2003, Methods Mol. Biol. 212: 189-195).

Given that current methods for diagnosing Turner syndrome are not sufficient to detect the condition in neonates, and detection in girls does is not accurate until an age when symptoms of Turner syndrome are already manifest, there exists a long felt need for assays and methods to detect Turner syndrome quickly, efficiently, accurately and early. The present invention meets this need.

BRIEF SUMMARY OF THE INVENTION

The present invention comprises a method for diagnosing a disorder of sexual differentiation in a human, the method comprising: contacting an isolated DNA sample from a human with a primer that specifically binds at a position adjacent to a single nucleotide polymorphism on an X chromosome of the human under conditions suitable for elongation of a nucleic acid complementary to said isolated DNA sample, elongating the nucleic acid complementary to the isolated DNA sample, wherein incorporation of a deoxynucleotide triphosphate into the complementary strand creates a detectable signal, wherein the detectable signal represents the presence of an allele, and detecting the loss of the allele, wherein the loss of the allele indicates loss of the X chromosome, thereby diagnosing a disorder of sexual differentiation in a human.

In one aspect of the present invention, the disorder of sexual differentiation is Turner syndrome.

In another aspect of the present invention, the isolated DNA sample is contacted with at least four primers.

In still another aspect of the present invention, the primers are selected from the group consisting of SEQ ID NOs: 26-48.

In yet another aspect of the present invention, the primers are selected from the group consisting of SEQ ID NO:26, SEQ ID NO:27, SEQ ID NO:28, SEQ ID NO:38, SEQ ID NO:32, SEQ ID NO:43, SEQ ID NO:33, SEQ ID NO:34, SEQ ID NO:39, SEQ ID NO:42, SEQ ID NO:47, SEQ ID NO:48 and SEQ ID NO:46.

In one aspect of the present invention, the human is selected from the group consisting of a human fetus, a female neonate, and a female child.

In still another aspect of the present invention, the female child is less than or equal to 10 years old.

The present invention also comprises a method for diagnosing a disorder of sexual differentiation in a human, the method comprising: contacting an isolated DNA sample from a human with a primer that specifically binds at a position adjacent to a single nucleotide polymorphism on an X chromosome of the human under conditions suitable for elongation of a nucleic acid complementary to said isolated DNA sample, elongating the nucleic acid complementary to the isolated DNA sample, wherein incorporation of a deoxynucleotide triphosphate into the complementary strand creates a detectable signal, wherein the detectable signal represents the presence of an allele; and, detecting the strength of the detectable signal, wherein the strength of the detectable signal is greater than 7.5% and less than 37.5% of the other detectable signal, said difference in strength of detectable signal indicates mosaicism in the X chromosome, thereby diagnosing a disorder of sexual differentiation in a human.

In one aspect of the present invention, the disorder of sexual differentiation is Turner syndrome.

In another aspect of the present invention, the isolated DNA sample is contacted with at least four primers.

In still another aspect of the present invention, the primers are selected from the group consisting of SEQ ID NOs: 26-48.

In yet another aspect of the present invention, the primers are selected from the group consisting of SEQ ID NO:26, SEQ ID NO:27, SEQ ID NO:28, SEQ ID NO:38, SEQ ID NO:32, SEQ ID NO:43, SEQ ID NO:33, SEQ ID NO:34, SEQ ID NO:39, SEQ ID NO:42, SEQ ID NO:47, SEQ ID NO:48 and SEQ ID NO:46.

In one aspect of the present invention, the human is selected from the group consisting of a human fetus, a female neonate, and a female child.

In still another aspect of the present invention, the female child is less than or equal to 10 years old.

The present invention encompasses a kit for diagnosing a disorder of sexual differentiation in a human, the kit comprising a primer that specifically binds at a position adjacent to a single nucleotide polymorphism on an X chromosome of an isolated human DNA sample, an applicator, and an instructional material for the use thereof. In one aspect of the present invention, the disorder of sexual differentiation is Turner syndrome.

In another aspect of the present invention, the isolated DNA sample is contacted with at least four primers.

In still another aspect of the present invention, the primers are selected from the group consisting of SEQ ID NOs: 26-48.

In yet another aspect of the present invention, the primers are selected from the group consisting of SEQ ID NO:26, SEQ ID NO:27, SEQ ID NO:28, SEQ ID NO:38, SEQ ID NO:32, SEQ ID NO:43, SEQ ID NO:33, SEQ ID NO:34, SEQ ID NO:39, SEQ ID NO:42, SEQ ID NO:47, SEQ ID NO:48 and SEQ ID NO:46.

In one aspect of the present invention, the human is selected from the group consisting of a human fetus, a female neonate, and a female child.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising

FIG. 3 is a table depicting the allele frequencies for the markers tested against DNA from different groups. Marker location and number are shown from pter (left) to qter (right) in the top two rows. SNP and relative nucleotide are depicted in rows 3 and 4. Karyotypes for each sample are in the left column. Numeric values represent relative allele signal strength (RAS). Shaded rows indicate abnormal genotypes. The top 3 samples from 45X females all show LOH (loss of heterozygosity), as do the 4 mosaic individuals. All other mosaic individuals were identified by this marker panel from the allele signal strength ratios.

FIG. 4, comprising FIG. 4A is a bar graph depicting the proportion of individuals demonstrating a LOH for all 10 markers tested (100% for 45x; 80% for 45X/46XX; 0% for 46 XX; p<0.0001, ANOVA). FIG. 4B is a bar graph depicting the proportion of individuals with a normal RAS (45-55%) for 1 to 5 of 10 markers tested. No 45X individual had any markers with a normal RAS value. Of 45X/46XX individuals, 6% had normal RAS values for 1 or 2 of 10 markers tested; none had normal RAS values for 3 or more markers. Of 46XX individuals, 6% had normal RAS values for only 1 or 2 of 10 markers tested; all others (88%) had normal RAS values for 3 or more markers. p<0.001, ANOVA).

FIG. 5 is a table depicting allele frequencies for markers tested against DNA from five different ethnic groups using 10 SNP markers. Marker numbers are shown from pter (left) to qter (right) in the top row. Each row represents DNA from an individual in the noted ethnic group. Numeric values represent relative allele strength. The right column depicts the karyotypic genotype. Using 2 SD to identify the boundaries for abnormal values, the normal range for relative signal strength is 45-55% (when two alleles are present). When one allele is present (LOH), normal values are 0-5.0%, and 95-100%. The column second from the right shows the number of heterogeneous markers for each subject. All markers revealed LOH for males; all 46XX females showed one or more heterogeneous markers in the normal range.

DETAILED DESCRIPTION OF THE INVENTION

Figure 1:
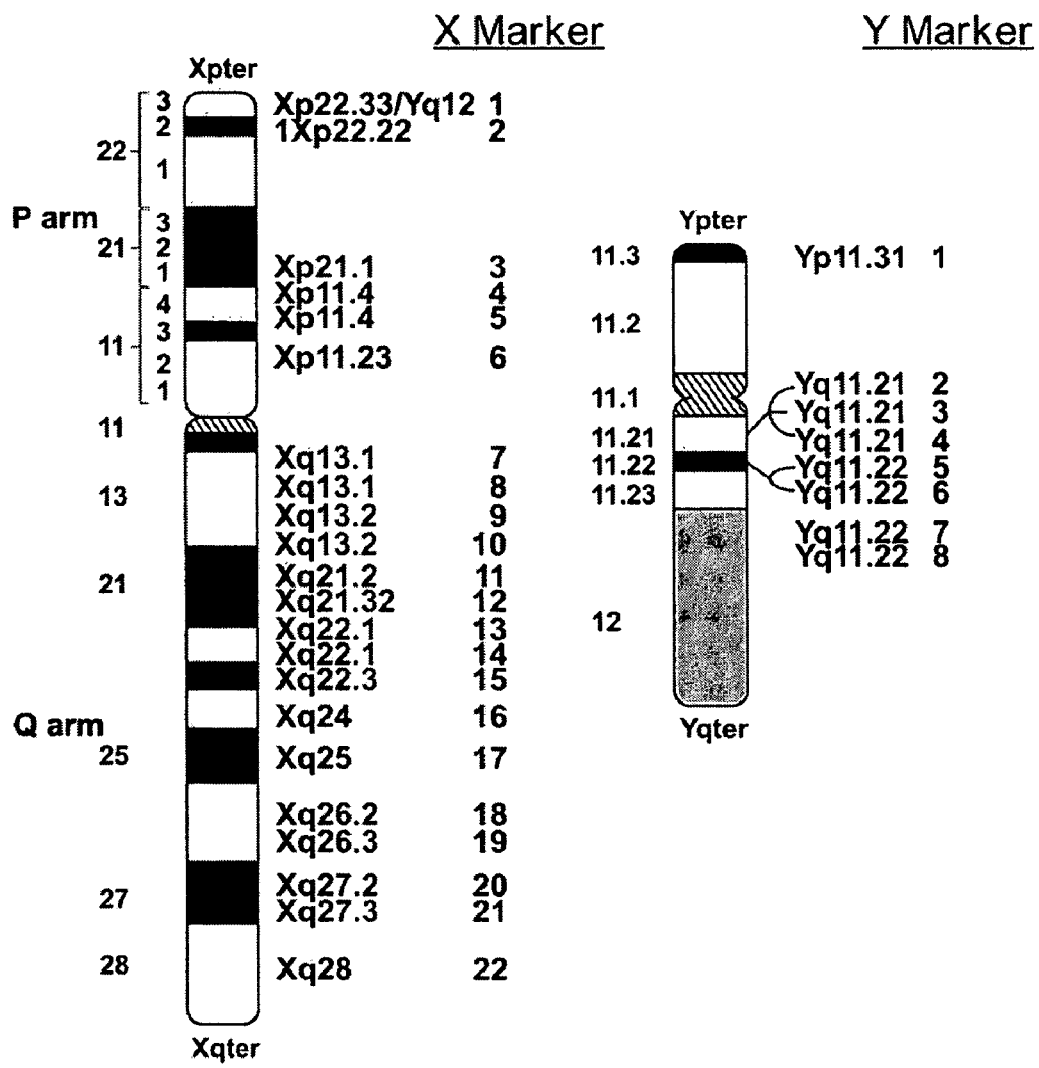
FIG. 1 is a schematic image of the location of X and Y chromosomes depicting the location of the markers tested.
Figure 2A:
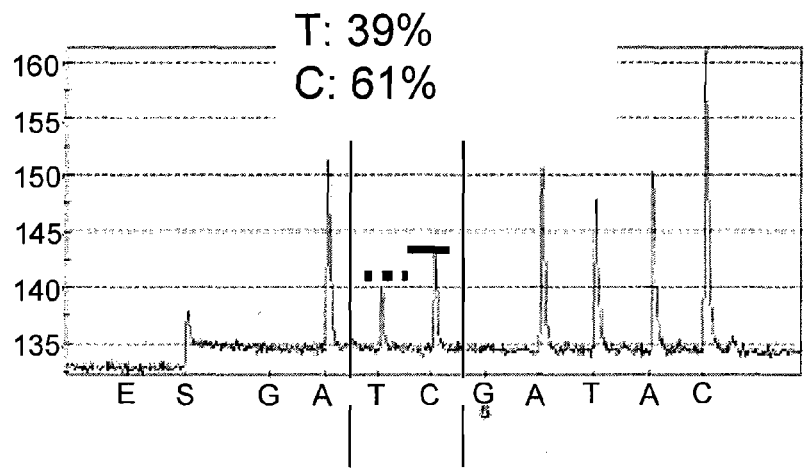
FIGS. 2A through 2D, is a series of pyrograms demonstrating that it is possible to distinguish Turner syndrome genotypes from normal genotypes by interrogating just one X-chromosome SNP. The Y-axis depicts signal strength; the X-axis depicts the SNP and flanking DNA sequence. Peaks correlate with intensity of a single nucleotide signal for each position shown. The dashed bar depicts intensity for the T allele; the solid bar shows intensity for the C allele. In the normal male (FIG. 2C: 46XY; C100%) and female with Turner syndrome due to 45X aneuploidy (FIG. 2D: 45X; T 100%), only one X-chromosome allele is present. In the normal female, 46XX, two X-chromosome alleles are present with equal signal intensity (FIG. 2B: T 50%; C 50%: p>0.5). In a girl who has Turner syndrome mosaicism comprising a mixture of 45X cells and cells with one normal X chromosome and one with a complex rearrangement (45X/46X,dic(X)(qter>p11::p11>qter), the alleles are not proportionately expressed (FIG. 2A: T 39%; C 61%; p<0.01).
Figure 2B:
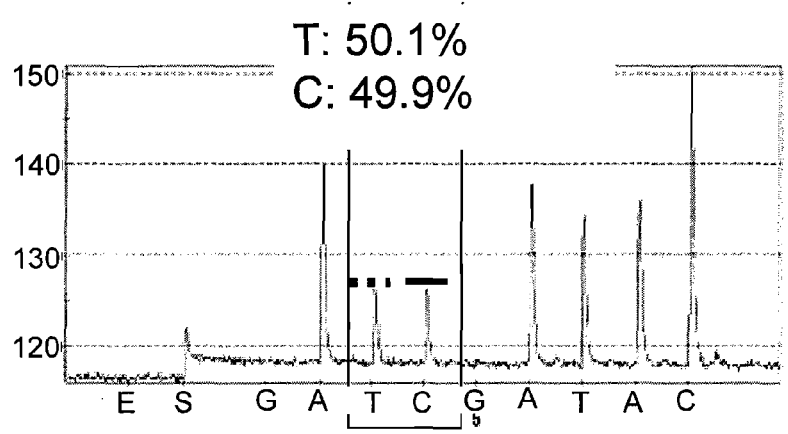
Figure 2C:
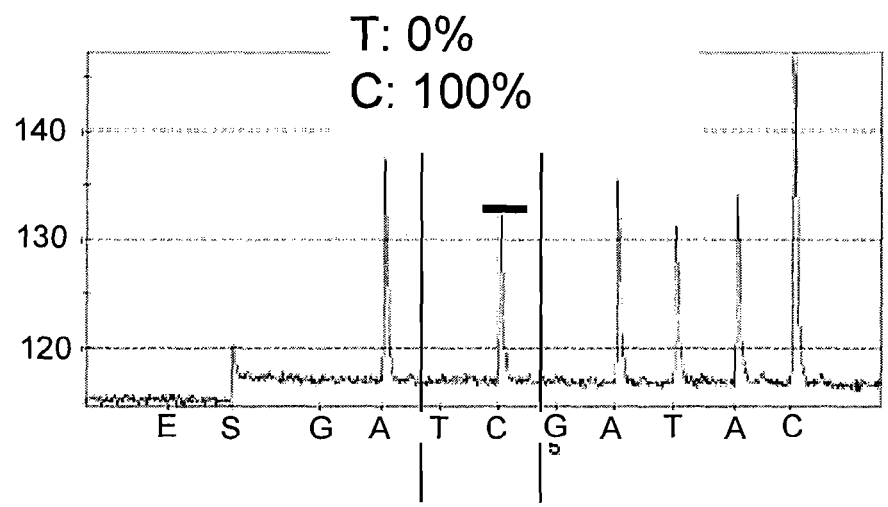
Figure 2D:
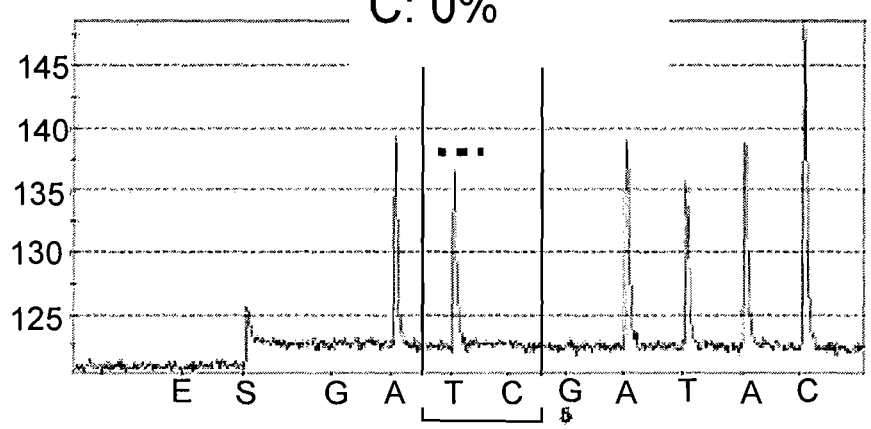
Figure 4A:
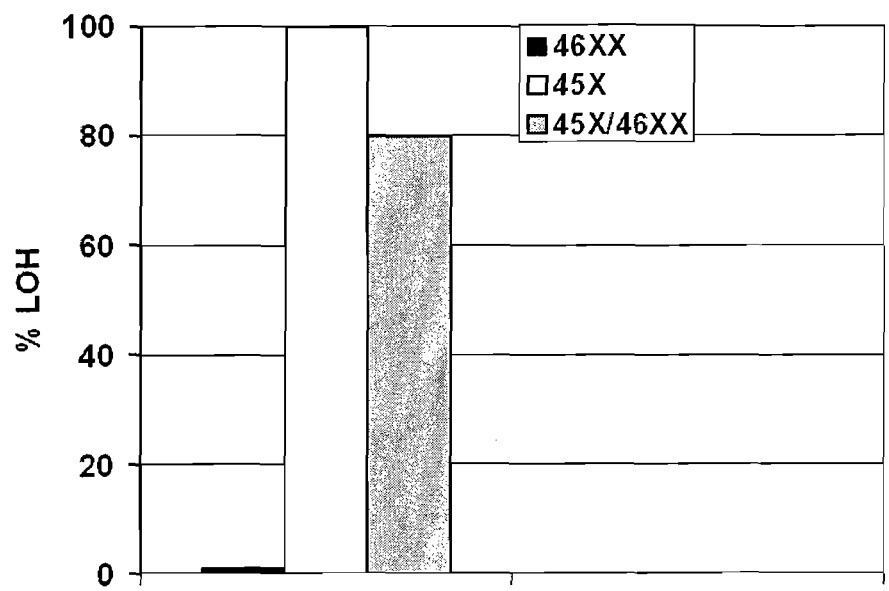
FIGS. 4A and 4B, is a series of graphs depicting the relative allele strength as related to the number of markers and genotype.
Figure 4B:
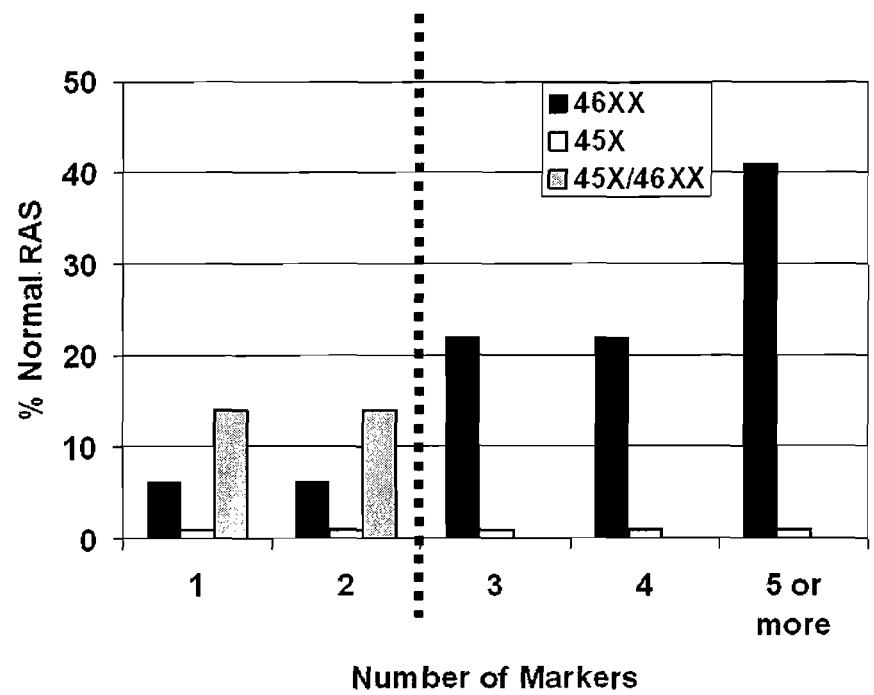
Figure 6:
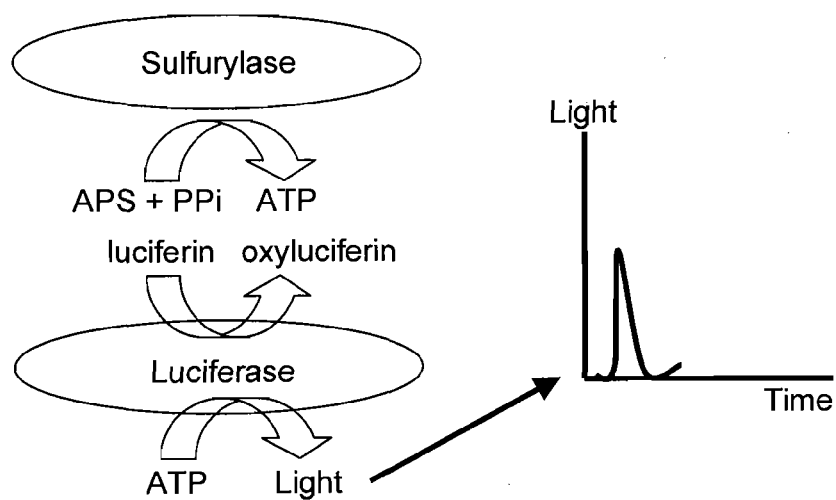
FIG. 6 is a schematic view of a pyrosequencing reaction and the generated pyrogram.
Figure 7:
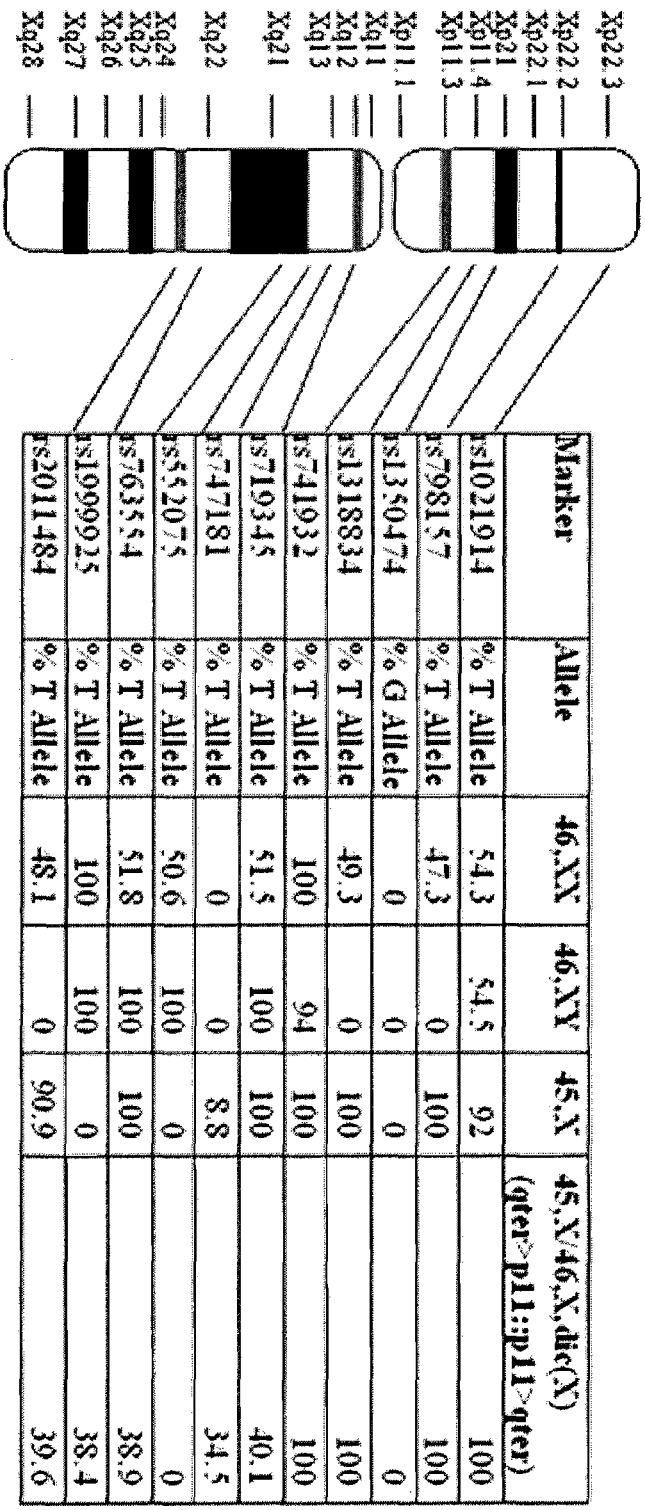
FIG. 7 is an image depicting the location of X-chromosome SNP markers and the results of pyrosequencing using 11 different markers to test four distinct DNA samples from a normal female (46XX), normal male (46XY), Turner syndrome due to X chromosome aneuploidy (45X), and Turner syndrome due to mosaicism (45X/46X,dic(X)(qter>p11::p11>qter). In the normal 46XX female (column 3), two alleles are equally present for 8 markers; 3 markers (rs1350474, rs741932, and rs1999925) are uninformative for this subject (homozygous for one allele). In the 46XY normal male (column 4), two alleles are detected for marker rs1021914, which corresponds to the X-chromosome pseudoautosomal region (the second allele comes from the pseudoautosomal region on the Y-chromosome); only one allele is detected using all other X-chromosome markers. In the 45X TS girl (column 5), LOH is seen with all markers (only one allele; ratio of 0 or 100%). In the TS girl with mosaicism and a complex X-chromosome rearrangement (column 6), LOH is observed with 6 markers, where the ratio of the two detectable alleles is less than 50% (34-40%) indicating an abnormal proportion of X-chromosome alleles from rs719345 through rs2011484, coincident with the deletion of the q-arm.

The present invention includes methods, kits and assays for the rapid, accurate, selective and sensitive detection of sex chromosome aneuploidy, mosaicism, and abnormalities by qualitative and quantitative single nucleotide polymorphism genotyping. That is, using the invention disclosed herein, one of skill in the art can rapidly and accurately identify anueploidies, mosaicism, and abnormal or missing human X and Y chromosomes, or extra copies of human X and Y chromosomes, at low cost.

As disclosed elsewhere herein, Turner syndrome is the most common genetic problem affecting women, and occurs when an X chromosome is completely deleted, portions of an X chromosome are deleted, or when chromosomal mosaicism occurs. Girls with Turner syndrome may also have occult Y chromosome sequences that are associated with an increased risk for germ cell tumors. Whereas some girls with Turner syndrome are identified in infancy or early childhood, many girls with Turner syndrome are not detected until after 10 years of age, resulting in delayed evaluation and treatment. To prevent the delayed recognition and treatment of Turner syndrome, the present invention comprises methods, kits and assays providing a quantitative method of genotyping that can be performed as part of newborn screening if needed, and can also be used at later stages of life for the diagnosis of Turner syndrome and other chromosome aneuploidy, mosaicism and abnormal human X and Y chromosomes.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

By the term "applicator" as the term is used herein, is meant any device including, but not limited to, a hypodermic syringe, a pipette, a buccal swab, and other means for using the kits of the present invention.

"Biological sample," as that term is used herein, means a sample obtained from a mammal that can be used to as a source to obtain nucleic acid from that mammal.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when corresponding positions in each of the molecules are occupied by nucleotides which normally base pair with each other (e.g., A:T and G:C nucleotide pairs).

As used herein, "disorders of sexual differentiation" means a condition in which the normal sex chromosome pairing is abnormal when compared to the normal sex chromosome pairings of 46XX or 46XY. Examples of disorders of sexual differentiation include Turner syndrome (45X0), Turner syndrome mosaicism (45X/46X where 46X is partially or completely deleted), Klinefelter Syndrome (47XXY), 47XXX, 47XYY, 48XXYY, 49XXXXY, 49XYYYY and other individuals with extra X and/or Y chromosomes. Disorders of sexual differentiation also include the conditions manifest in 46XY individuals with abnormal male gonadal or genital development, 46XX individuals with abnormal male gonadal or genital development, children with ambiguous gender at birth, and individuals with both testes and ovaries.

As used herein, an "instructional material" includes a publication, a recording, a diagram, or any other medium of expression, which can be used to communicate the usefulness of the nucleic acid, peptide, and/or composition of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container, which contains the nucleic acid, peptide, chemical compound and/or composition of the invention or be shipped together with a container, which contains the nucleic acid, peptide, chemical composition, and/or composition. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids, which have been substantially purified from other components, which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

Preferably, when the nucleic acid encoding the desired protein further comprises a promoter/regulatory sequence, the promoter/regulatory sequence is positioned at the 5' end of the desired protein coding sequence such that it drives expression of the desired protein in a cell. Together, the nucleic acid encoding the desired protein and its promoter/regulatory sequence comprise a "transgene."

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

"Mosaicism" is used herein to refer to a genotype wherein a proportion of cells have the normal compliment of genes (46XX), and a proportion of cells have an X-chromosome deletion (partial or complete).

A "polynucleotide" means a single strand or parallel and anti-parallel strands of a nucleic acid. Thus, a polynucleotide may be either a single-stranded or a double-stranded nucleic acid.

A "portion" of a polynucleotide means at least about fifteen to about fifty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

By the term "specifically binds," as used herein, is meant a primer that recognizes and binds a complementary polynucleotide, but does not recognize and bind other polynucleotides in a sample.

I. Methods

The present invention includes a method of screening for sex chromosome abnormalities. According to the methods of the present invention, a panel of informative single nucleotide polymorphism (SNP) markers that span the X chromosome are used in a pyrosequencing assay suitable for quantitative assessment of signal strength from single nucleotides. As demonstrated by the data disclosed herein, this panel of markers was designed and used to genotype 46XX, 46XY, 45X, and Turner syndrome mosaics, examining zygosity and signal strength for individual alleles. Pyrosequencing assays were also designed for the detection of Y chromosome material. With the use of only four SNP markers for the X chromosome, all Turner syndrome girls with 45,X, partial X chromosome deletions, or mosaicism were identified with 100% sensitivity. In mosaic individuals, Y chromosomal material was detected with 100% sensitivity. Therefore, the present invention encompasses a method of screening for Turner syndrome that due to its rapid nucleic acid-based nature, is amenable to inexpensive high-throughput screening for the detection of Turner syndrome and other sex chromosome disorders.

The present invention comprises a method of screening for and diagnosing sex chromosome aneuploidy using single nucleotide polymorphisms (SNP) that span the X and Y chromosomes. The present invention further comprises a method of screening for and diagnosing sex chromosome mosaicism using single nucleotide polymorphisms (SNP) that span the X and Y chromosomes. In another embodiment, the present invention encompasses a method of identifying sex chromosome aneuploidy using a qualitative assessment of SNP marker alleles on the X and Y chromosomes. In still another embodiment, the present invention encompasses a method of identifying sex chromosome mosaicism using a qualitative assessment of SNP marker alleles on the X and Y chromosomes. In addition, the present invention comprises a method of using specific genetic markers (i.e. SNPs) on the X chromosome for screening aneuploidy and mosaicism on the sex chromosomes. Preferably, the methods of the present invention are used for the screening, identification and/or diagnosis of Turner syndrome, but as disclosed elsewhere herein, the present invention is useful for screening, identifying and/or diagnosing other sex chromosome aneuploidies and mosaics.

The present invention can be used to detect Turner syndrome and other sex chromosome abnormalities detectable in disorders of sexual differentiation in a variety of tissues and other biological samples and for a variety of different purposes. As an example, for prenatal diagnosis of Turner syndrome, a biological sample of amniotic fluid, chorionic villous biopsy, fetal cells in maternal circulation, fetal blood cells extracted from an umbilical artery or vein, fetal cells from premortem or postmortem tissues, and fixed tissue can be used in the methods of the present invention. Methods for collecting such biological samples from a mother or a fetus are well known in the art and include amniocentesis, venous blood draws, and standard histology or pathology techniques.

The present invention can be used for the postnatal diagnosis of sex chromosome abnormalities, including, but not limited to Turner syndrome and other disorders of sexual differentiation, such as, for example, Klinefelter syndrome. However, according to the methods of the present invention, postnatal diagnosis can be performed before the point at which therapies for Turner syndrome, such as human growth hormone, are beyond an effective therapeutic window. That is, according to the methods of the present invention, screening, identifying and/or diagnosing Turner syndrome can be performed in infants, young girls, pre-pubescent girls, and the like. Further, as disclosed elsewhere herein, Turner syndrome can be diagnosed rapidly, sensitively, specifically and with minimum cost. This is because, as disclosed elsewhere herein, the methods of the present invention are an improvement over karyotyping and blood spot FSH measurement.

Postnatal diagnosis of Turner syndrome can be performed on a variety of biological samples, including, but not limited to blood, tissue or cells, DNA, plasma, serum, cerebrospinal fluid, sweat, urine, or any other body fluid, hair, skin, or mucosa tissue, bone, and stored or fixed tissues. Methods of collecting these tissues are well known in the art, and include, for example, phlebotomy, cheek swabs, biopsies, and standard techniques for collecting biological samples well known in the art.

In a preferred embodiment, the present invention is used to screen, identify and/or diagnose Turner syndrome. However, as disclosed elsewhere herein, the present invention can also be used to diagnose additional endocrine and genetic disorders, including, but not limited to, Klinefelter syndrome, aneuploidy and mosaicism of chromosome X, aneuploidy and mosaicism of chromosome Y, and the detection of Y chromosome material in X-chromosomes.

The present invention can also be used in the forensic sciences, such as for identifying bodies, establishing the identity of a body or a living person, and establishing the identity of a person claiming to be someone else. In addition, the present invention can be used in the field of epidemiology to establish the incidence or frequency of sex chromosome abnormalities in a population, including establishing gender frequency, establishing the frequency of sex chromosome aneuploidy, and detecting Turner syndrome patients at increased risk for gonadal tumors by having Y chromosomal material. The present invention can also be used to determine sex assignment by genotype, for example, in sporting events and competitions, identification, insurance or employment-related purposes, psychological counseling and gender assignment.

In addition, the present invention can be used as a means of differential diagnosis for eliminating or confirming the etiology behind another medical condition and confirming the presence or absence of sex chromosome abnormalities, including Turner syndrome as a cause. As an example, the present invention can be used to confirm or eliminate a sex chromosome abnormality, such as Turner syndrome when short stature, excessive height, early, delayed, or troubled menarche, early, delayed, or troubled puberty, infertility, cryptorchidism, a risk of malignancy (cancer) due to gonadal dysgenesis, and other malignant conditions are present.

The present invention comprises isolating a nucleic acid sample from a biological sample and screening the nucleic acid sample for Turner syndrome or another sex chromosome abnormality. The nucleic acid sample being analyzed is any type of nucleic acid in which potential SNPs exist. For instance, the nucleic acid sample may be an isolated genome or a portion of an isolated genome. An isolated genome consists of all of the DNA material from a particular organism, i.e., the entire genome. A portion of an isolated genome, which is referred to as a reduced complexity genome (RCG), is a plurality of DNA fragments within an isolated genome but which does not include the entire genome. Genomic DNA comprises the entire genetic component of a species excluding, applicable, mitochondrial DNA.

Thus, the present invention provides a novel method for detecting sex chromosome abnormalities using informative SNP markers spanning the X and Y chromosomes, followed by quantitative assessment of allele signal strength via pyrosequencing. Further, the invention disclosed herein comprises the simultaneous qualitative assessment of allele heterozygosity and quantitative assessment of allele signal from a panel of single nucleotide polymorphism (SNP) markers distributed over human chromosomes X and Y.

A preferred sequencing method for SNPs is pyrosequencing. See, for instance, Ahmadian et al., (2000, Anal. Biochem, 280:103-110; Alderborn et al., 2000, Genome Res. 10:1249-1258 and Fakhrai-Rad et al., 2002, Hum. Mutat. 19:479-485). Pyrosequencing involves a cascade of four enzymatic reactions that permit the indirect luciferase-based detection of the pyrophosphate released when DNA polymerase incorporates a dNTP into a template-directed growing oligonucleotide. Each dNTP is added individually and sequentially to the same reaction mixture, and subjected to the four enzymatic reactions. Light is emitted only when a dNTP is incorporated, thus signaling which dNTP in incorporated. Unincorporated dNTPs are degraded by apyrase prior to the addition of the next dNTP. The method can detect heterozygous individuals in addition to heterozygotes. Pyrosequencing uses single stranded template, typically generated by PCR amplification of the target sequence. One of the two amplification primers is biotinylated thereby enabling streptavidin capture of the amplified duplex target. Streptavidin-coated beads are useful for this step. The captured duplex is denatured by alkaline treatment, thereby releasing the non-biotinylated strand. The detection primer used for SNP identification using pyrosequencing is designed to hybridize to a sequence 3' to the SNP. In a preferred embodiment, the 3' sequence is adjacent, or more preferably, immediately adjacent to the SNP position. Thus, the SNP identity is ascertained when the first nucleotide is incorporated. Pyrosequencing can detect heterozygotes, as disclosed elsewhere herein.

Pyrosequencing is used in the methods of the present invention to diagnose a disorder of sexual differentiation, preferably Turner syndrome in a human, preferably a human female fetus, neonate (infant) or child, and other children with disorders of sexual differentiation. Preferably, the child is less than 10 years old so that therapeutic action can be taken before short stature and other complications of Turner syndrome become permanent. The method of the present invention comprises contacting a DNA sample obtained from the biological sample of a human with a primer that specifically binds at a position adjacent, or immediately adjacent, to an SNP on the X chromosome of the human under conditions suitable for elongation of a nucleic acid complementary to the isolated DNA sample. Conditions suitable for elongation of a complementary nucleic acid are similar or identical to those used for PCR reactions and are described elsewhere herein. In addition, suitable conditions are described in the manufacturer's protocol for pyrosequencing machines (Biotage AB, Uppsala, Sweden).

The complementary nucleic acid is elongated as described for the pyrosequencing reaction described elsewhere herein. The incorporation of each deoxynucleotide triphosphate into the complementary strand creates a detectable signal (e.g. light). The presence of a detectable signal is captured by a camera and converted into a signal that represents an allele. As demonstrated by the data disclosed herein, (e.g. FIG. 2), the absence of a signal where a signal would exist in a 46XX human indicates loss of the allele, which is indicative of loss of the X chromosome, thereby providing a diagnosis for Turner syndrome.

Pyrosequencing is also used in the methods of the present invention to diagnose a disorder of sexual differentiation, preferably Turner syndrome, in a human, preferably a human female fetus, neonate (infant) or child. That is, the present invention can be used to diagnose Turner syndrome due to loss of heterozygosity or due to X chromosome mosaicism. The method of the present invention comprises contacting a DNA sample obtained from the biological sample of a human with a primer that specifically binds at a position adjacent, or immediately adjacent, to an SNP on the X chromosome of the female under conditions suitable for elongation of a nucleic acid complementary to the isolated DNA sample. Conditions suitable for elongation of a complementary nucleic acid are similar or identical to those used for PCR reactions and are described elsewhere herein.

As demonstrated by the data disclosed elsewhere herein, if the relative allele strength, as measured by the detectable signal emitted by the pyrosequencing reaction, differs by greater than 7.5% and less than 37.5% for an SNP, that difference in relative allele strength indicates mosaicism in the X chromosome, and thus, Turner syndrome.

The X-chromosome markers useful in the methods, assays and kits of the present invention comprise, but are not limited to those listed in the tables below.

| X-Chromosome Marker | Extension Primer |
|---|---|
| rs798157 (#2) (SEQ ID NO: 3) | GGCCAGTTGAAATACTAATA (SEQ ID NO: 26) |
| rs2107419 (SEQ ID NO: 4) | CCTTGTAAACCTCTCTTGTG (SEQ ID NO: 27) |
| rs1021914 (#1) (SEQ ID NO: 5) | GGTAGAAATTACTGCAGC (SEQ ID NO: 28) |
| rs1350474 (#3) (SEQ ID NO: 6) | GGTTCAATAAGCTCAGAACT (SEQ ID NO: 29) |
| rs1318834 (#4) (SEQ ID NO: 7) | TGTCCACATGAAATTCTG (SEQ ID NO: 30) |
| rs747181 (#7) (SEQ ID NO: 8) | GAGATGCCAGAAGTTCA (SEQ ID NO: 31) |
| rs552075 (#9) (SEQ ID NO: 9) | ATCTGTGCGACTTCTCA (SEQ ID NO: 32) |
| rs763554 (#11) (SEQ ID NO: 10) | TAATCCTTCTTTGCAAGC (SEQ ID NO: 33) |
| rs2011484 (#13) (SEQ ID NO: 11) | TTGACACTAGTCAGTATCTA (SEQ ID NO: 34) |
| rs1298577 (#15) (SEQ ID NO: 12) | ATGAGGAGCATGTGGA (SEQ ID NO: 35) |
| rs932465 (#18) (SEQ ID NO: 13) | TCAGCAGCCTTCTAAAT (SEQ ID NO: 36) |
| rs741932 (#6) (SEQ ID NO: 14) | GACACTTCTTTCCTGCGGC (SEQ ID NO: 37) |
| rs719345 (#8) (SEQ ID NO: 15) | CATGGAAGTTATAAAGGCT (SEQ ID NO: 38) |
| rs1475971 (#14) (SEQ ID NO: 16) | GGGGTTGTTGTCAAATAGTA (SEQ ID NO: 39) |
| rs1999925 (#12) (SEQ ID NO: 17) | ATATGCTCTTGGTCAATTC (SEQ ID NO: 40) |
| rs729496 (#16) (SEQ ID NO: 18) | AGTGGGGTTTGGAGACT (SEQ ID NO: 41) |
| rs1012539 (#17) (SEQ ID NO: 19) | CTGGTTAGGGAAACAA (SEQ ID NO: 42) |
| rs575348 (#10) (SEQ ID NO: 20) | CTTCCCTCTTTCTGTGAG (SEQ ID NO: 43) |
| rs206037 (#5) (SEQ ID NO: 21) | GTCTTTTAAATTTGTAGTTC (SEQ ID NO: 44) |
| rs708580 (#21) (SEQ ID NO: 22) | ATTTGCTCAGTCAAAATATG (SEQ ID NO: 45) |
| rs717377 (#22) (SEQ ID NO: 23) | GGCAGCCAAGGGGAG (SEQ ID NO: 46) |
| rs1429617 (#19) (SEQ ID NO: 24) | TGCCCTCTACTAATGTCAC (SEQ ID NO: 47) |
| rs881222 (#20) (SEQ ID NO: 25) | GCTGTGGATATACCCCTTA (SEQ ID NO: 48) |

| Y-Chromosome Marker | Extension Primer |
|---|---|
| rs2032665 (#2) (SEQ ID NO: 49) | CATATATTAATAAGAAGTCA (SEQ ID NO: 59) |
| rs2072422 (#4b) (SEQ ID NO: 50) | CAGTTTATAGGTCAAATATC (SEQ ID NO: 60) |

-continued

| | |
|---|---|
| rs2032635 (#6)<br>(SEQ ID NO: 51) | CTTAAAGCAACTTAAAAATG<br>(SEQ ID NO: 61) |
| rs2032631 (#7)<br>(SEQ ID NO: 52) | TCAGAAGGAGCTTTTTGC<br>(SEQ ID NO: 62) |
| rs1558843 (#5)<br>(SEQ ID NO: 53) | AATAGCTGCCAAGTAAAAT<br>(SEQ ID NO: 63) |
| rs2032595<br>(SEQ ID NO: 54) | GTATGTGTTGGAGGTGAG<br>(SEQ ID NO: 64) |
| rs2032624 (#4)<br>(SEQ ID NO: 55) | TTCAAGGGCATTTAGAAC<br>(SEQ ID NO: 65) |
| rs2032625 (#8)<br>(SEQ ID NO: 56) | GAAGTTGGAGGATTC<br>(SEQ ID NO: 66) |
| rs2032598 (#3)<br>(SEQ ID NO: 57) | GCCAGCAATTTAGTATTGCC<br>(SEQ ID NO: 67) |
| rs2253109 (#1)<br>(SEQ ID NO: 58) | GCTTGCAATATTAAGTGCC<br>(SEQ ID NO: 68) |

The panel of markers of the present invention can be used in a first-pass screening that, as demonstrated by the data disclosed herein, detects 99% of Turner syndrome anueploidies and mosaics. The initial screen is confirmed using a second panel of ten SNP markers, which can comprise eight SNP markers from chromosome X and two from chromosome Y. However, as demonstrated by the data disclosed herein, detecting only four X chromosome SNP markers identified all girls with 45,X, partial X chromosome deletions or mosaicism with 100% sensitivity. In addition, in these mosaic individuals, Y chromosome material was detected with 100% sensitivity. Preferably X-chromosome markers 2, 4, 5, 8, 9, 10, 11, 13, 14, 17, 18, 19, 20 and 22 are detected using primers having SEQ ID NOS: 26, 27, 28, 38, 32, 43, 33, 34, 39, 42, 47, 48 and 46.

The presence or absence of sex chromosome abnormalities, including Turner syndrome, aneuploidy, mosaicism is determined by genotyping using the SNP markers disclosed herein. Specifically, small segments (50 to 500 base pairs) of genomic DNA are amplified by polymerase chain reaction (PCR) using oligonucleotides complementary to unique sequences flanking the ten SNP markers disclosed herein and used in the initial screening panel. To assess both qualitative heterozygosity and quantitative signal from polymorphic alleles at each SNP marker, genotyping is performed by pyrosequencing.

Pyrosequencing, as described above, comprises a series of steps for the accurate and qualitative analysis of DNA sequences. Pyrosequencing comprises hybridizing a sequencing primer to a single stranded, PCR amplified, DNA template, and incubating the primers and DNA template with the standard PCR enzymes (e.g. DNA polymerase) with ATP sulfurylase, luciferase and apyrase, and the substrates, adenosine 5' phosphosulfate (APS) and luciferin. The first of four deoxyribonucleotide triphosphates (dNTPs) is added to the reaction as a second step. DNA polymerase catalyzes the incorporation of the deoxyribo-nucleotide triphosphate to the complementary base in the target DNA template strand. Each incorporation event is accompanied by release of pyrophosphate (PPi) in a quantity equimolar to the amount of incorporated nucleotide. In the third step, ATP sulfurylase quantitatively converts PPi to ATP in the presence of APS. This ATP drives the luciferase mediated conversion of luciferin to oxyluciferin and generates visible light proportional to the amount of ATP. The light produced in the luciferase-catalyzed reaction is detected by a charge coupled device (CCD) camera and seen as a peak in a Pyrogram™. The height of each peak (light signal) is proportional to the number of nucleotides incorporated. As a fourth step, apyrase, a nucleotide degrading enzyme, continuously degrades ATP and unincorporated dNTPs. This reaction switches off the light and regenerates the reaction solution. The next dNTP is then added one at a time and the process is repeated for each dNTP (i.e. dCTP, dGTP, dTTP) in the fifth step. Deoxyadenosine alfa-thio triphosphate (dATPaS) is used as a substitute for deoxyadenosine triphosphate (dATP) since it is efficiently used by the DNA polymerase, but not recognized by the luciferase. As the process continues, the complementary DNA strand is built up and the nucleotide sequence is determined from the signal peaks in the Pyrogram. Pyrosequencing analytical software assigns both genotype and quantifies the signal strength of each allele. Genotype and signal strength are outputted to standard spreadsheet format. Methods for accomplishing pyrosequencing reactions are well known in the art and are described in, for example, U.S. Pat. No. 6,258,568 and 6,258,568. Kits, apparatuses and reagents for pyrosequencing are commercially available from, for example, Biotage Ab, Uppsala, Sweden).

Using the data developed from the genotyping reaction, the biological sample can be assessed for aneuploidy and/or mosaicism. As an example, genotype assignments for the X-chromosome markers are assessed for heterozygosity over the entire X chromosome for each subject. For any 46XX female subject the likelihood of loss of heterozygosity in 1 through 10 SNP markers—assuming a heterozygosity value of 0.2 for each marker—is provided in the following table:

| Number of X markers<br>with loss of heterozygosity | Likelihood of occurring<br>in 46XX female* |
|---|---|
| 1 | $2.0 \times 10^{-1}$ |
| 2 | $4.0 \times 10^{-2}$ |
| 3 | $8.0 \times 10^{-3}$ |
| 4 | $1.6 \times 10^{-3}$ |
| 5 | $3.2 \times 10^{-4}$ |
| 6 | $6.4 \times 10^{-5}$ |
| 7 | $1.3 \times 10^{-5}$ |
| 8 | $2.6 \times 10^{-6}$ |
| 9 | $5.1 \times 10^{-7}$ |
| 10 | $1.0 \times 10^{-7}$ |

The presence of mosaicism is evaluated and assessed by determining the ratio of signal strength from each 2-allele system for every SNP marker. Assuming a normal distribution around the mean, ratios that differ from 50% or 100% by 0.5 standard deviations (SD) are suggestive of X-chromosome mosaicism and are flagged as such. As an example, a heterozygote genotype should have equal, or 50% signal from each allele. If one allele provides <35% or >65% of the total signal then mosaicism is possible. If this occurs in at least two of the SNP markers then mosaicism is likely. In the case of a homozygote genotype (e.g. Turner syndrome), then 100% of the signal should come from a single allele. If less than 85% of the signal comes from one allele, then mosaicism is possible.

In order to determine the presence of Y chromosomal material, and thus the increased risk for gonadal tumors, genotype assignments for the markers of Y chromosomal material are used to screen DNA as described above. As demonstrated by the data disclosed herein, the Y chromosome markers disclosed herein, preferably, the Y chromosome marker Nos. 1, 3, 4, 5, 6 and 7 are used to identify Y chromosomal material in 46XY males and individuals with Turner syndrome with Y chromosomal material. Y chromosome markers are preferably identified using primers having the SEQ ID NOS: 68, 67, 65, 63, 61 and 62.

For individual screening procedures, such as for girls with short stature or late-onset puberty, the present invention and the kits described herein are useful in the context of a pediatric endocrinology clinic.

Samples are procured after informed consent is obtained from the patient and/or parent. A buccal swab or other biological sample can be collected after the patient is instructed how to obtain the buccal swab or a practioner obtains the swab or other biological sample. DNA in bucall swabs remains stable over long periods of time, facilitating transport and storage. Buccal swabs can be collected using the commercially available Catch-All™ swab (Epicentre® Madison, Wis.), which typically yields up to 5 μg of DNA from a single pass along the inner cheek. Various methods of extracting DNA from a biological sample, including the Qiagen Bio-Sprint 96 DNA Blood kit, are used to extract the DNA from the biological sample.

The DNA isolated from the patient is the subject to pyrosequencing genotyping. Pyrosequencing can initially involve a panel of 10 X-chromosome markers (X-panel-A: markers 2, 5, 8, 9, 11, 14, 18, 19, 20 and 22) and one 1 Y-chromosome marker, preferably marker 1, 3, 4, 5, 6 or 7. The 10 X-panel-A was selected from the markers identified elsewhere herein. The Y-chromosome marker only detects Y-chromosomal material.

For high-throughput testing, samples can be prepared and formatted using an automated pipettor (e.g. a Hydra 2-plus-1 semi-automated liquid handling system with nanoliter pipettor, Matrix Technologies, Natick, N.H.) to dispense reaction components into 96-well plates. DNA amplification can be performed on a thermal cycler (e.g. an ABI 9700 96-well dual block thermal cycler (ABI, Foster City, Calif.)).

For the PCR amplification, a biotinylated primer is added to 20 ng of template DNA, Taq Gold buffer (Applied Biosystems, Foster City, Calif., USA), MgCl$_2$, 200 nmol each primer, 100 nmol dATP, dCTP, dGTP, dTTP, and 0.5 units AmpliTaq Gold DNA polymerase (Applied Biosystems), for a total volume of 20 microliters in a 96-well format. One cycle of denaturation (95° C. for 10 minutes) is followed by 45 cycles of PCR (94° C. for 30 seconds, 55° C. for 30 seconds, 72° C. for 30 seconds), and finally extension at 72° C. for 10 minutes.

Pyrosequencing is then performed on the sample. Biotinylated single-strand DNA fragments are generated by mixing the PCR product with streptavidin-coated paramagnetic beads and processed according to the manufacturer's instructions (Pyrosequencing Sample Preparation; Pyrosequencing AB, Uppsala, Sweden). An automated pyrosequencing instrument, is used. Pyrosequencing analytical software (PSQ 96HS SNP Software) is used to quantify the signal strength of each allele and assess genotype. Genotype and relative allele signal strength are exported to a standard spreadsheet format.

The pyrosequencing data is measured using the following criteria. A relative allele signal strength between 45 and 55% is normal. A relative allele strength of >95% or <5.0% is indicative of LOH. Relative allele strengths between 5 and 45%, and between 55 and 95%, are abnormal and demonstrate unequal allele expression. These criteria are used for each marker to assess if there is LOH or normal or abnormal allele signal strength.

As demonstrated by the data disclosed herein, with only 3 informative makers, 46XX females can be distinguished from Turner syndrome (45X, mosaicism, or partial X-chromosome deletion) (p<0.001; ANOVA). Therefore, if heterozygosity is observed for 4 or more markers, samples need not be rescreened. If samples demonstrate LOH in 7 of the 10 SNPs, they are rescreened with another 10 X-chromosome SNPs (X-panel-B). If the rescreened samples demonstrate LOH using 7 of the new 10 markers (X-panel-B), the genotype is considered abnormal. These samples can then be screened with a panel of 6 Y-chromosome markers (Y-panel-A) to assess if Y-chromosomal material is present.

Based on pyrogram data, genotypes are assigned by assessing if there is LOH and abnormal allele frequency. If an LOH is observed in a majority of the SNPs identified herein, the sample will be considered abnormal.

As an example of population screening tests, many state departments of public health, or the equivalent local or federal agencies, collect heel prick blood samples from newborn children on filter paper discs to screen for inborn metabolism errors. These samples can be used in the methods of the present invention to detect sex chromosome abnormalities in both males (i.e. Kleinfelter Syndrome (47XXY), females, and other individuals with disorders of sexual differentiation.

Whether for individual or population testing for Turner syndrome, DNA is extracted from a human biological sample. Methods for collecting DNA from a human biological sample are well known in the art, and can included the use of various commercial kits, such as the Qiagen BioSprint 96 DNA Blood kit, which can be automated for high-throughput use. Preferably, the extracted DNA is free of protein, nucleases, and other contaminants or inhibitors, which is suitable for direct use in downstream applications such as PCR and pyrosequencing.

The samples are then pyrosequenced as described elsewhere herein. Further, as demonstrated by the data disclosed herein, a difference in relative allele signal strength between 45 and 55% is normal. Relative allele strength of >95% or <5.0% is indicative of LOH. Relative allele strengths between 5 and 45%, and between 55 and 95%, are abnormal and indicate unequal allele expression.

If samples are observed to show LOH in 7 of the 10 samples using X-panel-A, they are rescreened with another 10 X chromosome markers (X-panel-B) in single reactions. Conversely, if heterozygosity is observed for 4 or more markers, samples are not rescreened. If the rescreened samples are observed to show LOH using 7 of the new 10 markers, the genotype is considered abnormal. These samples are then screened with a panel of Y-chromosome markers to assess if Y chromosomal material is present.

II. Kits

The invention encompasses various kits relating to screening, identifying and/or diagnosing Turner syndrome in an individual and assessing the sex chromosomes that are present in individuals with disorders of sexual differentiation. Although exemplary kits are described below, the contents of other useful kits will be apparent to the skilled artisan in light of the present disclosure. Each of these kits is included within the invention. The kits of the present invention are useful, because, as disclosed elsewhere herein, such kits can be used to diagnose, among other sex chromosome abnormalities, Turner syndrome in a human. As disclosed elsewhere herein, diagnosis of Turner syndrome can lead to early treatment of short stature, earlier detection of gonadal tumors, prevention or treatment of otitis media, supplemental education for communication problems, and the like.

The kits of the present invention can be used to perform population screening or individual screening of a newborn, a fetus, or a child. This is because, as disclosed elsewhere herein, the present methods can be used for the early diagnosis of Turner syndrome and other sex chromosome disorders at young ages. As demonstrated for a number of inborn errors of metabolism, this can be achieved by newborn screening.

The present invention comprises a kit useful for screening for Turner syndrome. The kit of the present invention can comprise primers that specifically bind to the X and Y chromosome markers disclosed elsewhere herein for diagnosis of Turner syndrome in various clinical labs. The present invention further comprises kits for the collection of a biological sample. A patient or practitioner can collect a biological sample and send the sample to a clinical lab where the present screen for Turner syndrome is performed.

The present invention further comprises DNA collection kits for detecting Turner syndrome mutations. The kits of the present invention can comprise reagents and materials to expedite the collection of samples for DNA extraction and analysis. These kits can comprise an intake form with a unique identifier, such as a bar-code, a sterile biological collection vessel, such as a Catch-All™Swab (Epicentre® Madison, Wis.) for collecting loose epithelial cells from inside the cheek; and an instruction material that depicts how to properly apply the swab, dry it, repack it and return to a clinical lab. The kit can further comprise a return postage-paid envelope addressed to the clinical lab to facilitate the transport of biological samples.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Many girls with Turner syndrome are not detected until they are teenagers. The penalty of untimely diagnosis includes delayed treatment and a less favorable outcome (Saenger, 1997, Curr. Ther. Endocrinol. Metab., 6: 239-243; Bertelloni, et al., 2003, J. Pediatr. Endocrinol. Metab., 16(Suppl 2): 307-315; Saenger, et al., 2001, J. Clin. Endocrinol. Metab., 86: 3061-3069). The data disclosed herein demonstrate that screening for Turner syndrome using qualitative and quantitative genotyping by pyrosequencing is an effective means for detecting Turner syndrome at a much earlier stage.

Quantitative fluorescent PCR (QF-PCR), which is based on the PCR amplification of selected chromosome specific short tandem nucleotide repeats (STRs), has been adapted for the assessment of X chromosome anueploidies (Cirigliano, et al., 1999, Prenat. Diagn. 19: 1099-1103). However, this method has limited ability to differentiate quantitative differences in signal strength from different alleles. Thus the 50% of Turner syndrome girls with X chromosome mosaicism or partial deletions are not identified using this approach. In comparison, the present data demonstrate that using pyrosequencing to genotype SNPs provides a comprehensive diagnostic screening strategy that identifies all causes of Turner syndrome, including mosaicism and partial deletions.

Example 1

Detection of Turner Syndrome Genotypes in Human Patients Turner Syndrome Genotypes Genotypes for more than 1,000 girls with Turner syndrome have been reported (Hall and Gilchrist, 1990, Pediatr. Clin. North Am., 37: 1421-1440; Uehara, et al., 2001, J. Hum. Genet., 46: 126-131; Henn and Zang, 1997, Nature 390: 569; Kleczkowska, et al., 1990, Genet. Couns. 1: 227-233; Lippe and Saenger, 2002, In: Sperling Mass., ed. Pediatric Endocrinology. Philadelphia: Saunders, 519-564; Tsezou, et al., 1999, Clin. Genet., 56: 441-446; Gunther, et al., 2004, Pediatrics 114: 640-644). Compiling these studies, the relative proportions of the different genotypes are presented in Table 1. Each of these genotypes have been tested using the methods of the present invention, and Turner syndrome has been detected with 100% accuracy with for each genotype, as demonstrated below.

TABLE 1

Incidence of Cytogenetic findings in girls with Turner syndrome.

| % | Karyotype |
|---|---|
| 55 | 45, X |
| 17 | 46, X, i(Xq) |
| 13 | 45, X/46XX |
| 5 | 46, X, r(X) |
| 5 | 45, X/46XY |
| 2.5 | 46, XXq- |
| 2 | 46, XXp- |
| 2 | 45, X/47XXX |
| 0.5 | 46, X, (X:15) |

Pyrosequencing

Pyrosequencing involves six steps (Elahi and Ronaghi, 2004, Methods Mol. Biol., 255: 211-220; Fakhrai-Rad, 2002, Hum. Mutat. 19: 479-485; Ronaghi, 2003, Methods. Mol. Biol., 212: 189-195; Pourmand, et al., 2002, Nucleic Acids Res., 30: e31). First, a sequencing primer is hybridized to a single stranded, PCR-amplified DNA template, and incubated with DNA polymerase, ATP sulfurylase, luciferase and apyrase, and the substrates, adenosine 5' phosphosulfate (APS) and luciferin. Second, the first of four deoxynucleotide triphosphates (dNTP) is added to the reaction. DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. Third, ATP sulfurylase quantitatively converts PPi to ATP in the presence of adenosine 5' phosphosulfate. This ATP drives the luciferase-mediated conversion of luciferin to oxyluciferin, which generates visible light in amounts that are proportional to the amount of ATP. The light produced in the luciferase-catalyzed reaction is detected by a charge coupled device (CCD) camera and seen as a peak in a pyrogram. Each light signal is proportional to the number of nucleotides incorporated. Fourth, apyrase, a nucleotide-degrading enzyme, continuously degrades unincorporated dNTPs and excess ATP. When degradation is complete, another dNTP is added. Fifth, addition of dNTPs is performed one at a time. Deoxyadenosine alfa-thio triphosphate (dATPαS) is used as a substitute for the natural deoxyadenosine triphosphate (dATP) since it is efficiently used by the DNA polymerase, but not recognized by the luciferase. Sixth, as the process continues, the complementary DNA strand is elongated and the nucleotide sequence is determined from the signal peak in the pyrogram. Pyrograms are then analyzed using proprietary software to determine DNA sequence and assign alleles.

DNA Samples

DNA samples were obtained from the human genetic cell repository of the National Institute of General Medical Sciences (NIGMS/NIH) maintained at the Coriell Institute for Medical Research (Camden, N.J.). The karyotype of each sample was determined by the Coriell Institute (depicted in the table in FIG. 3).

Genotyping

Pyrosequencing was used to genotype each genomic DNA sample for SNP markers. Oligonucleotide primer pairs were designed for the PCR amplification of unique DNA flanking each SNP. The reverse primer for all pairs was synthesized with a 5'-T3 tag sequence extension (5'-ATTAACCCTCACTAAAGGGA-3'; SEQ ID NO:1). In addition to the forward and reverse PCR primers, a universal 5'-biotinylated T3 primer (5'-ATTAACCCTCACTAAAGGGA-3'; SEQ ID NO:2) was added to each PCR reaction. Amplicon sizes ranged from 88-210 and 168-493 base pairs for the X chromosome and Y chromosome markers. Biotinylated PCR products were generated in a 20 µl PCR reaction containing 10 ng of genomic DNA, 0.4 units of Hotstart Taq polymerase (Qiagen, Valencia, Calif.), 4 picomoles of forward PCR primer, 0.4 picomoles of reverse PCR primer, 3.6 picomoles of biotinylated T3 primer, 2.5 mM $MgCl_2$, and 200 µM each of dATP, dCTP, dGTP, and dTTP. Thermal cycling was conducted in an Applied Biosystems (Foster City, Calif.) 96-well PCR block (15 minutes at 95° C.; 45 cycles of 30 seconds at 95° C., 45 seconds at 56° C., 60 seconds at 72° C.; 5 minutes at 72° C.; and a hold at 4° C. Upon completion of PCR, the biotinylated PCR product from the entire reaction was purified by binding to Streptavidin-Sepharose (Amersham, Piscataway, N.J.) using per a standard protocol (Biotage AB, Uppsala, Sweden). The resulting single stranded template was annealed with the extension primer for 2 minutes at 80° C., cooled to room temperature and sequenced in a PSQ96MA Pyrosequencing instrument. PSQ96MA® analysis software (version 2.0.2) automatically scored the quality of each reaction, assigned genotypes, and measured the peak heights of each allele. Genotype and signal strength was exported to a standard spreadsheet format. The operator who did the pyrosequencing and related analysis was blinded to genotype. After data was tabulated was it compared with provided genotypes.

Statistics

Mean±SD values were calculated using Graph Pad Prism (San Diego, Calif.).

The results of the experiments set forth in this Example are now described.

Turner Syndrome Study Population

More than 50 girls with Turner syndrome have been actively examined over the course of the study. 90% of these girls are being treated with growth hormone. When ages at diagnosis are examined, 10% of the girls had obvious clinical manifestations of Turner syndrome at birth, leading to diagnosis in the neonatal period. However, the vast majority of girls were not diagnosed until 12.2±2.3 years when they were referred for evaluation of short stature or delayed pubertal development. The mean age when treatment with growth hormone was started was 12.7±2.1 years. Unfortunately, 15% of the girls with Turner syndrome were referred after epiphyseal fusion had occurred, precluding growth hormone treatment.

National Cooperative Growth Study (NCGS) data involving 2,798 girls with Turner syndrome revealed a similar national trend (Parker, et al., 2003, J. Pediatr., 143: 133-135; Plotnick, et al., 1998, Pediatrics 102: 479-481). The average age of girls with Turner syndrome at initiation of growth hormone therapy is 10.1±3.6 years. Thus nationwide, the vast majority of girls with Turner syndrome are diagnosed in the second decade of life, although comprehensive studies of this issue are unavailable.

Development of a PCR/Pyrosequencing-Based Assay for Sex Chromosome Screening

A novel, pyrosequencing-based method for sex-chromosome screening was developed that is vastly more quantitative than previously developed QF-PCR methods. The approach involves simultaneous qualitative assessment of allele heterozygosity and quantitative assessment of allele signal strength from a panel of SNP markers distributed through chromosomes X and Y. For the X-panel, 22 SNPs spanning the X-chromosome from Xp22 to Xq28 were selected (FIG. 1), with heterozygosity values >25% from the dbSNP database (National Library of Medicine, Bethesda, Md.). For the Y-panel, 8 SNPs spanning Yp11.31 through Yq1.22 were selected (FIG. 1).

Assessment of Specificity for Turner Syndrome

To assess the utility of pyrosequencing for determining X-chromosome allele heterozygosity, the variance and specificity for each SNP on DNA samples from 9 unrelated members of CEPH pedigrees without Turner syndrome was calculated. DNA samples were obtained from the human genetic cell repository of the National Institute of General Medical Sciences (NIGMS/NIH) maintained at the Coriell Institute for Medical Research (Camden, N.J.).

In the normal male (46XY; C100%) and female with Turner syndrome (45,X; T 100%), only one X-chromosome allele is present. In the normal female, two alleles are present with equal signal intensity (T 50%; C 50%: P>0.5). In a girl who is a Turner syndrome mosaic with a complex X-chromosome rearrangement, the alleles are not proportionately expressed (T 39%; C 61%; p<0.01).

To assess both qualitative heterozygosity and quantitative signal strength from polymorphic alleles at each SNP marker, genotyping was performed by pyrosequencing. Small segments (50 to 500 basespairs) of genomic DNA were amplified by PCR using oligonucleotide pairs complementary to unique non-proprietary sequences flanking the 22 X chromosome SNP markers. The pyrosequencing analytical software (PSQ 96MA SNP Software) was then used to quantify the signal strength of each allele and assign genotype. Genotype and signal strength were then exported to standard spreadsheet format and compared with the known karyotype.

Relative allele signal strength (RAS) was determined for each marker relative to three possible genotype outcomes: A+B allele equally present (expected A50%/B50%), A allele present (A100%; B 0%); B allele present (A0%; B100%) (Table 2).

Results obtained from the 22 X-chromosome SNPs depicted in FIG. 1 and tested on 12 46XX DNA samples genotypes (n=12) are depicted in Table 2. For 17 of the SNPs, two alleles were detected among the different individuals. One SNP was from the pseudoautosomal region of the X-chromosome (SNP 1), and two (SNPs 3 and 16) had duplicated PCR targets (two sites in the genome by BLAST search). When A/B alleles were both present (exclusive of markers 1, 3 and 16), the relative signal strength was 50.5%±2.5% (mean±SD) for each allele. Based on this analysis, when both alleles are present, a difference in relative signal strength of 5% represented a greater than 2 SD difference. When only one allele was present (A or B; loss of heterozygosity, LOH), the relative allele signal strength was 99.8%±0.3% if the allele was present, and 0.2%±0.1% if the allele was absent. However, to allow for consideration of possible "noise" at the extreme of dynamic range of the CCD camera, the variance is adjusted to 5% at the extremes in accordance with the manufacturer's recommendations. Thus, a value between 95-100% represents one allele, and 0-5% is indicative of an absent allele (confidence interval 99.9%, p<0.001). These studies have characterized and now disclose 14 SNPs that can be used as informative markers for assessing heterozygosity along the length of the X chromosome.

TABLE 2

Percent allele signal strength using 22 X-chromosome markers against 46XX DNA when both alleles are present.

| X-Marker | A/B allele | X-Marker | A/B allele |
| --- | --- | --- | --- |
| 1 pa | 54.3 ± 1.4 | 12 | ND |
| 2* | 50.9 ± 3.5 | 13* | 48.0 ± 2.8 |
| 3 dup | 50.6 ± 1.5 | 14* | 50.8 ± 2.6 |
| 4* | 56.8 ± 3.3 | 15 | ND |
| 5* | 50.3 ± 1.7 | 16 dup | 62.9 ± 9.0 |
| 6 | ND | 17* | 49.5 ± 0.9 |
| 7 | ND | 18* | 49.5 ± 2.1 |
| 8* | 52.5 ± 1.9 | 19* | 49.6 ± 1.2 |
| 9* | 51.9 ± 1.8 | 20* | 52.0 ± 1.2 |
| 10* | 52.0 ± 2.1 | 21 | ND |
| 11* | 50.7 ± 3.0 | 22* | 52.2 ± 1.9 |

Note:
Values are mean ± SD;
ND = two alleles not detected in any sample;
pa = pseudoautosomal region of X-chromosome;
dup = PCR amplifies duplicated target (two distinct sites in genome identified by BLAST search);
Asterisk depicts informative markers.

Assessment of Sensitivity for Detecting Turner Syndrome and Abnormal Sex Chromosomes in Disorders of Sexual Differentiation The utility of the use of the identified SNPs to detect Turner syndrome was then tested. A collection of DNA samples was collected from individuals with Turner syndrome and other sex chromosome abnormalities from the National Institute of General Medical Sciences (Table 3).

PCR reactions were set-up and pyrosequencing was performed according to the manufacturer's specifications and the protocols disclosed above. Because a difference in relative allele signal strength of 5% is 2 SD from the mean, the threshold was set at >5% for detecting an absent X-chromosome. The absence of one allele was also assessed (LOH; relative frequency >95% or <5.0%).

TABLE 3

Cell lines from individuals with Turner syndrome and other sex chromosome abnormalities Cytogenetic Diagnosis 45, X
45, X/46, X, del(X)(pter > q11:)
45, X/46, X, del(Y)(pter > q11.2:)
45, X/46, X, I(X)(qter > cen > qter)
45, X/46, X, del(Y)(pter > q11.2:)

TABLE 3-continued

Cell lines from individuals with Turner syndrome and other sex chromosome abnormalities Cytogenetic Diagnosis 45, X/46, X, del(X)(qter > cen:)/46, X, I(X)(qter > cen > qter)
45, X/46, X, I(X)(qter > cen > qter)
45, X, dic(Y; 5)(Ypter > Yq12:: 5p15.1 > 5qter).ish dic(Y; 5) (DYZ1+, DYZ3+, D5S23−)
45, X/46, X, dic(X)(qter > p11::p11 > qter)
46, X, dic(X)(qter > p11::p11 > qter), inv(2)(pter > p11::q13 > p11::q13 > qter)
46, X, I(X)(qter > cen > qter)
46, X, I(X)(qter > cen > qter)
46, X, +frag/46, X, I(Y)(qter > cen > qter)
46, X, add(X).ish del dup(X)(wcpX+, cdy16c07−).rev ish del dup(X)
46, X, del(X)(pter > 21.3::21.1 > qter)
46, X, t(X; 21)(Xqter > Xp21::21p12 > 21pter; 21qter > 21p12::Xp21 > Xpter)
46, XX, inv ins(6)(pter > p21.3::q13 > q15::p21.3 > q13::q15 > qter)/47, XXX, inv ins(6)(p21.3; q15q13)
47, XXY
47, XXY
47, XXX
48, XXYY
48, XXYY
49, XXXXY
47, XXX
47, XYY
49, XYYYY Assessment for Aneuploidy If an individual has only one X-chromosome (hemizygous for the X-chromosome), then all markers spanning the length of the chromosome will demonstrate LOH. Thus, genotype assignments for the 14 markers shown to be informative above were assessed for heterozygosity over the entire X-chromosome for each subject. Using this approach, all the DNA samples with 45X karyotype were identified with 100% sensitivity (FIG. 3).

Assessment of Mosaicism

Detection of X-chromosome mosaicism was assessed by quantifying the relative signal strength of each amplified allele. When a variety of different Turner syndrome mosaics were examined, and defining a difference >5% in relative allele signal strength was defined as abnormal, it was discovered that all 14 SNPs identified Turner syndrome mosaicism. Overall, a combination of a minimum of just four markers (for example 11, 14, 18 and 19) unequivocally identified 100% of girls with Turner syndrome mosaicism. (FIG. 3).

Assessment of Y-Chromosomal Material

In addition to testing for X-chromosome SNPs, 8 Y-chromosome markers were tested in 22 XY male, 9 XX females and in all Turner syndrome samples. Using this approach, each marker could identify all 46XY males (100% sensitivity). There was no detection of Y-chromosomal material in any 46 XX female (100% selectivity), and Y chromosomal material was detected in each of the Turner syndrome genotypes known to have Y-chromosomal material by karyotype (100% sensitivity).

In summary, these observations demonstrate the development of a DNA-based Turner syndrome screening program that can detect all of the reported Turner syndrome genotypes.

Analysis of Selectivity

For the screening test disclosed herein to be useful, false-positive rate should be very low (high selectivity). An analysis of the selectivity of the present screening test estimates the false-positive rate to be less than 0.2%.

To address this issue, DNA from an additional 60 cell lines with normal karyotypes was tested using the SNP marker panel (Table 4). Because the United States is a multiracial country of individuals of many different genetic backgrounds, there are differences in SNP frequencies among different racial groups that could confound the utility of the present test when applied to diverse populations. Thus, DNA from different racial groups was screened to assess if there are limitations in the present marker sets or whether the threshold for defining abnormal test results in different racial groups needs to be readjusted.

TABLE 4

NIGMS HGCR Human Variation Panels.

AFRICAN AMERICAN PANEL
CARIBBEAN
CAUCASIAN PANEL
CHINESE
PUERTO RICAN

PCR reactions were set-up and pyrosequencing was performed using markers 2, 5, 8, 9, 11, 14, 18, 19, 20, and 22. As above, a difference in relative allele signal strength between 45 and 55% is normal. Relative allele strength of >95% or <5.0% is indicative of LOH. Relative allele strengths between 5 and 45%, and between 55 and 95% are abnormal and indicate unequal allele expression.

Heterozygosity was detected with at least 1 of 10 markers in normal females (46XX) and LOH for 46XY normal males for all markers (FIG. 5). When markers revealed two alleles in females, relative signal strengths for each allele were 50.5±1.1 (range 45-55). Of the 10 markers tested, only 1 of 10 markers was informative in 3% of 46XX females, only 2 of 10 markers were informative in 10% females, 3 of 10 markers in 20% of females, 4 of 10 markers in 20% of females, and 5 or more of 10 markers were informative in 50% of females. Thus in normal 46XX females, 4.1±0.6 (mean±SD) markers were informative for heterozygosity in the normal range (45-55% relative allelic frequency).

When the same 10 markers were tested on DNA from individuals with Turner syndrome, LOH for all markers was observed in 100% of 45X females with Turner syndrome (n=12). Of Turner syndrome females with mosaicism or partial X-chromosome deletion (n=16), 1 of 10 markers showed heterozygosity in the normal range (45-55) in 1 of the Turner syndrome females, and 2 of 10 markers showed heterozygosity in the normal range in 2 of the Turner syndrome females. In none of the Turner syndrome females with mosaicism or partial X-chromosome deletion did 3 or more markers show heterozygosity in the normal range. Thus in Turner syndrome females 0.3±0.5 (mean±SD) markers revealed a heterozygosity score within the normal range (45-55% relative allelic frequency) (p<0.0001 vs non-Turner syndrome; ANOVA). Thus, there is no overlap among females with 3 or more markers demonstrating heterozygosity in the normal range in Turner syndrome due to monosomy, mosaicism or partial X-chromosome deletions.

When relative allele signal strength was assessed for each marker on 46XX DNA samples from different ethnic groups, no significant differences were observed. Similarly, when relative allele signal strength was assessed for each marker among individuals with or without Turner syndrome among different ethnic groups, no significant differences were observed.

These data support the utility of applying the present set of markers in ethnically diverse populations. Importantly, using just three informative markers, 46XX female can be distinguished from 45X individuals with Turner syndrome, and those individuals with Turner syndrome due to mosaicism and partial X-chromosome deletions. Each of the markers tested has a similar likelihood of detecting allele differences in individuals without Turner syndrome.

DNA Samples

Figure 8:
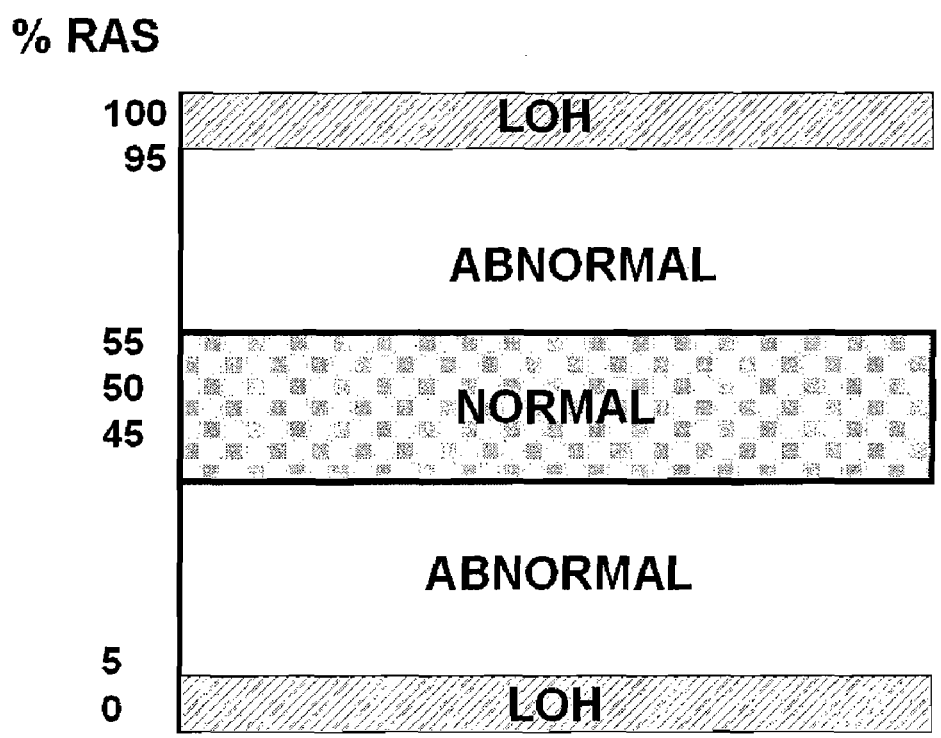
FIG. 8 is a bar graph depicting the criteria used to evaluate pyrosequencing data. Relative allele strength (RAS)>95% or <5.0% is indicative of LOH. RAS between 45% and 55% is normal (99.9% confidence interval). RAS between 5-45%, and 55-95% are abnormal and indicate unequal allele relative signal strength.

FIG. 3 is a table describing the allele frequencies for markers tested against DNA from different genotypes. The depicted markers represent 10 of the 15 informative markers. The marker location and number are shown from pter (left) to qter (right) in top two rows. SNP and relative nucleotide are shown in rows 3 and 4. Karyotypes for each sample are in the left column. Numeric values represent relative allele frequency. When two alleles are present, the normal relative frequency is 50.5±2.5% (mean±SD). Using 3 SD to identify abnormal values, the normal relative frequency range is 42.5-57.5% (two alleles present). When one allele is present (LOH), normal values are 0-5.0%, and 95-100%. Thus when two alleles are present relative allele frequencies between 5-42.5% and 57.5% and 95% are considered abnormal (Table 2 and FIG. 8). It is also abnormal to only have one allele with multiple markers. In all cases when Y chromosomal material was present, it was detected by 6 or more Y markers. The top 3 samples from 45,X females all show LOH, as do 4 mosaic individuals. All other mosaic individuals were identified as abnormal by this marker panel from abnormal allele frequency ratios.

Assessment of X Chromosome Markers

To assess both qualitative heterozygosity and quantitative signal strength at each SNP, genotyping was performed by pyrosequencing DNA samples from nine 46,XX females and eight 46,XY males from the Center d'Etude du Polymorphisme Humain (CEPH, Paris, France) pedigree 1331. For each bi-allelic SNP marker the frequencies of the three possible genotypes were determined: A/B, A/A, and B/B (Table 2).

Overall, 17 of the 22 markers were heterozygous (column A/B) in at least one 46,XX subject. Of these 17, one marker was from a known pseudoautosomal region of the X chromosome (marker 1), and one marker behaved like it resides in a pseudoautosomal region although searching against the reference human genome sequence produced only one significant match (marker 16). Thus, at least 15 SNP markers, widely distributed over the X chromosome, were informative for interrogating non-mosaic 45,X Turner syndrome subjects.

To identify Turner syndrome mosaics, the ratios of A-allele and B-allele signal strength were determined for each marker relative to three possible genotype outcomes: A+B allele equally present (expected: A50%/B50%), A-allele present only (expected: A100%/B0%), and B-allele present only (expected: A0%/B100%).

When A/B alleles were both present (exclusive of markers 1 and 16), the relative ratio of signal strength from each allele was 50.5±2.5% (mean±SD). When both alleles were present, a ratio of greater than or less than 7.5% from the mean (<43 or >58) represents three standard deviations (3 SD). When only the A-allele was present (A100%/B0%), the mean ratio was 99.8±0.1%. When only the B-allele was present (A 0%; B100%), the mean ratio was 100±0. Based on this analysis, two alleles in 46,XX individuals could be detected using markers 2, 4, 5, 8, 9, 10, 11, 13, 14, 17, 18, 19, 20, and 22.

Assessment of Sensitivity for Detecting Turner Syndrome

To test the utility of the X chromosome marker panel in identifying Turner syndrome, a collection of 25 DNA samples from subjects with Turner syndrome and other sex chromosome abnormalities was assembled from the National Institute of General Medical Sciences (FIG. 3) and genotyped by Pyrosequencing. First, the ability of the marker panel to detect loss of heterozygosity (LOH) in non-mosaic 45,X Turner syndrome samples was assessed. FIG. 3 depicts that for the three 45,X samples (rows 6-8), there was not a single heterozygote genotype. The odds that no heterozygote could be detected in 46,XX females with 15 consecutive X chromosome markers is $1:(0.3)^{15}$ (or about 1 in 10 million), assuming a heterozygosity value of 0.3 for each marker.

Next, the ability of the marker panel to detect Turner syndrome mosaics by quantifying the relative signal strength of each SNP allele was examined. When a variety of different Turner syndrome mosaic DNA samples were examined with the X-chromosome SNP panel, 18 of the 22 markers identified Turner syndrome mosaicism as defined by a difference of >3 SD in relative allele signal strength (FIG. 3). A combination of a minimum of just four markers (for example 11, 14, 18 and 19) identified 100% of the 13 samples with Turner syndrome mosaicism (rows 9-21).

The SNP panels disclosed herein, when combined with quantitative genotyping, can identify many different kinds of X and Y chromosomal problems, not just Turner syndrome; these include 47,XXY causing Klinefelter syndrome, translocations, ring chromosome, marker chromosomes, inversions, insertions, isochromes, duplications, dicentric chromosomes, derivative chromosomes, deletions, and complex anueploidies. Thus whereas the present data discloses the use of the panel for detecting Turner syndrome, the present testing approach will identify other disorders of sex chromosomes, including 46,XY females and 46,XX males. As such, neonatal screening for Turner syndrome and other complex conditions involving sex chromosomes and sexual differentiation is now possible using a quantitative genotyping approach.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed:

1. A method for diagnosing Turner syndrome in a human female subject comprising:
pyrosequencing bi-allelic single nucleotide polymorphisms (SNPs) using informative primers consisting of SEQ ID NO: 26-48, wherein said primers specifically bind to a position adjacent to said SNPs and said SNPs collectively span the X-chromosome;
determining the relative allele strength for each allele by said pyrosequencing; and diagnosing Turner Syndrome in said subjects wherein a relative allele strength for all alleles tested is less than 5% or greater than 95%.

2. The method of claim 1, wherein said human is selected from the group consisting of a fetus, a neonate, and a child.

3. The method of claim 2, wherein said child is less than or equal to 10 years old.

* * * * *

SEQUENCE LISTING

```
<160> NUMBER OF SEQ ID NOS: 68

<210> SEQ ID NO 1
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 1
attaaccctc actaaaggga                                                 20

<210> SEQ ID NO 2
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 2
attaaccctc actaaaggga                                                 20

<210> SEQ ID NO 3
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t

<400> SEQUENCE: 3
aggccagttg aaatactaat atacgnatga attggagatt aattttaagg a              51

<210> SEQ ID NO 4
```

```
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or g
<220> FEATURE:
<221> NAME/KEY: misc_feature
<222> LOCATION: (26)..(26)
<223> OTHER INFORMATION: n is a, c, g, or t

<400> SEQUENCE: 4
aatgatggtt tcagatgtgt aaattncaca agagaggttt acaaggccat c            51

<210> SEQ ID NO 5
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t

<400> SEQUENCE: 5
tgggtgggta gaaattactg cagcangtac aaaactgtcc ttcatgccat a            51

<210> SEQ ID NO 6
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or g
<220> FEATURE:
<221> NAME/KEY: misc_feature
<222> LOCATION: (26)..(26)
<223> OTHER INFORMATION: n is a, c, g, or t

<400> SEQUENCE: 6
aaaggttcaa taagctcaga actgtntaat ttccaatctt ttataattat t            51

<210> SEQ ID NO 7
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t

<400> SEQUENCE: 7
aaaaatgtcc acatgaaatt ctgcangcag tcgcaggtgt tcactcgctc c            51

<210> SEQ ID NO 8
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t
```

<400> SEQUENCE: 8
agatatgaga tgccagaagt tcagangcag aagaaaaggg taggtttaac a        51

<210> SEQ ID NO 9
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t

<400> SEQUENCE: 9
ctgcagcatc tgtgcgactt ctcagngcat tgactccttt agccacacac c        51

<210> SEQ ID NO 10
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t

<400> SEQUENCE: 10
ctttcctaat ccttctttgc aagcanatac cattcataag tcacataatt a        51

<210> SEQ ID NO 11
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or g
<220> FEATURE:
<221> NAME/KEY: misc_feature
<222> LOCATION: (26)..(26)
<223> OTHER INFORMATION: n is a, c, g, or t

<400> SEQUENCE: 11
gaggcaaatc ggtaggctag gaactntagt agatactgac tagtgtcaag a        51

<210> SEQ ID NO 12
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or g
<220> FEATURE:
<221> NAME/KEY: misc_feature
<222> LOCATION: (26)..(26)
<223> OTHER INFORMATION: n is a, c, g, or t

<400> SEQUENCE: 12
cttcaatctt ttttcagtta cttacntctc cacatgctcc tcatctgcat c        51

<210> SEQ ID NO 13
<211> LENGTH: 51
<212> TYPE: DNA
<213> ORGANISM: Homo sapiens
<220> FEATURE:
<221> NAME/KEY: misc_feature

```
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t

<400> SEQUENCE: 13
agtcttttca gcagccttct aaatangttt ctgttcaaag aaataatggg a           51

<210> SEQ ID NO 14
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t

<400> SEQUENCE: 14
ctgacacttc tttcctgcgg ccccanagcg ggctcccttta ctactggaat g           51

<210> SEQ ID NO 15
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or g
<220> FEATURE:
<221> NAME/KEY: misc_feature
<222> LOCATION: (26)..(26)
<223> OTHER INFORMATION: n is a, c, g, or t

<400> SEQUENCE: 15
ttaaagacta ataagaagg caatcncaga gcctttataa cttccatgat t           51

<210> SEQ ID NO 16
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or g
<220> FEATURE:
<221> NAME/KEY: misc_feature
<222> LOCATION: (26)..(26)
<223> OTHER INFORMATION: n is a, c, g, or t

<400> SEQUENCE: 16
atcacctctc agtcctaact gttctntgat actatttgac aacaacccca g           51

<210> SEQ ID NO 17
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or g
<220> FEATURE:
<221> NAME/KEY: misc_feature
<222> LOCATION: (26)..(26)
<223> OTHER INFORMATION: n is a, c, g, or t

<400> SEQUENCE: 17
caagggataa tagaagtaca caaacntgaa ttgaccaaga gcatatataa a           51
```

```
<210> SEQ ID NO 18
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or g
<220> FEATURE:
<221> NAME/KEY: misc_feature
<222> LOCATION: (26)..(26)
<223> OTHER INFORMATION: n is a, c, g, or t

<400> SEQUENCE: 18
actcagtgtc ttctcttggg cttctnagtc tccaaacccc actccatccc a              51

<210> SEQ ID NO 19
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t

<400> SEQUENCE: 19
cagctgggct ggttagggaa acaaanggtc aaatgcaatt ctcgaggatg c              51

<210> SEQ ID NO 20
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t

<400> SEQUENCE: 20
tcacttccct ctttctgtga gtagantcta tagctctgtg ctttgagctc a              51

<210> SEQ ID NO 21
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t

<400> SEQUENCE: 21
tgtcttttaa atttgtagtt ctatanggaa agaattgatg tccactctat a              51

<210> SEQ ID NO 22
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or g
<220> FEATURE:
<221> NAME/KEY: misc_feature
<222> LOCATION: (26)..(26)
<223> OTHER INFORMATION: n is a, c, g, or t
```

<400> SEQUENCE: 22
taagtaagtc aaatataatg attttncata ttttgactga gcaaatgata t          51

<210> SEQ ID NO 23
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t

<400> SEQUENCE: 23
caaccagtgg gcagccaagg ggagangaca tctcaaagtg gcttgtagat t          51

<210> SEQ ID NO 24
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or g
<220> FEATURE:
<221> NAME/KEY: misc_feature
<222> LOCATION: (26)..(26)
<223> OTHER INFORMATION: n is a, c, g, or t

<400> SEQUENCE: 24
tctggatgga gtcaaatgtc attctntggt gacattagta gagggcataa t          51

<210> SEQ ID NO 25
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or g
<220> FEATURE:
<221> NAME/KEY: misc_feature
<222> LOCATION: (26)..(26)
<223> OTHER INFORMATION: n is a, c, g, or t

<400> SEQUENCE: 25
atgttttaac ataaaatcaa atggcntaag gggtatatcc acagcctaag t          51

<210> SEQ ID NO 26
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 26
ggccagttga aatactaata                                              20

<210> SEQ ID NO 27
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 27
ccttgtaaac ctctcttgtg                                              20

```
<210> SEQ ID NO 28
<211> LENGTH: 18
<212> TYPE: DNA
<213> ORGANISM: Artificial Sequence
<220> FEATURE:
<223> OTHER INFORMATION: Chemically Synthesized Primer

<400> SEQUENCE: 28
ggtagaaatt actgcagc                                              18

<210> SEQ ID NO 29
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 29
ggttcaataa gctcagaact                                            20

<210> SEQ ID NO 30
<211> LENGTH: 18
<212> TYPE: DNA
<213> ORGANISM: Artificial Sequence
<220> FEATURE:
<223> OTHER INFORMATION: Chemically Synthesized Primer

<400> SEQUENCE: 30
tgtccacatg aaattctg                                              18

<210> SEQ ID NO 31
<211> LENGTH: 17
<212> TYPE: DNA
<213> ORGANISM: Artificial Sequence
<220> FEATURE:
<223> OTHER INFORMATION: Chemically Synthesized Primer

<400> SEQUENCE: 31
gagatgccag aagttca                                               17

<210> SEQ ID NO 32
<211> LENGTH: 17
<212> TYPE: DNA
<213> ORGANISM: Artificial Sequence
<220> FEATURE:
<223> OTHER INFORMATION: Chemically Synthesized Primer

<400> SEQUENCE: 32
atctgtgcga cttctca                                               17

<210> SEQ ID NO 33
<211> LENGTH: 18
<212> TYPE: DNA
<213> ORGANISM: Artificial Sequence
<220> FEATURE:
<223> OTHER INFORMATION: Chemically Synthesized Primer

<400> SEQUENCE: 33
taatccttct ttgcaagc                                              18

<210> SEQ ID NO 34
<211> LENGTH: 20
<212> TYPE: DNA
<213> ORGANISM: Artificial Sequence
<220> FEATURE:
```

<223> OTHER INFORMATION: Chemically Synthesized Primer

<400> SEQUENCE: 34
ttgacactag tcagtatcta                                                         20

<210> SEQ ID NO 35
<211> LENGTH: 16
<212> TYPE: DNA
<213> ORGANISM: Artificial Sequence
<220> FEATURE:
<223> OTHER INFORMATION: Chemically Synthesized Primer

<400> SEQUENCE: 35
atgaggagca tgtgga                                                             16

<210> SEQ ID NO 36
<211> LENGTH: 17
<212> TYPE: DNA
<213> ORGANISM: Artificial Sequence
<220> FEATURE:
<223> OTHER INFORMATION: Chemically Synthesized Primer

<400> SEQUENCE: 36
tcagcagcct tctaaat                                                            17

<210> SEQ ID NO 37
<211> LENGTH: 19
<212> TYPE: DNA
<213> ORGANISM: Artificial Sequence
<220> FEATURE:
<223> OTHER INFORMATION: Chemically Synthesized Primer

<400> SEQUENCE: 37
gacacttctt tcctgcggc                                                          19

<210> SEQ ID NO 38
<211> LENGTH: 19
<212> TYPE: DNA
<213> ORGANISM: Artificial Sequence
<220> FEATURE:
<223> OTHER INFORMATION: Chemically Synthesized Primer

<400> SEQUENCE: 38
catggaagtt ataaaggct                                                          19

<210> SEQ ID NO 39
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 39
ggggttgttg tcaaatagta                                                         20

<210> SEQ ID NO 40
<211> LENGTH: 19
<212> TYPE: DNA
<213> ORGANISM: Artificial Sequence
<220> FEATURE:
<223> OTHER INFORMATION: Chemically Synthesized Primer

<400> SEQUENCE: 40
atatgctctt ggtcaattc                                                          19

```
<210> SEQ ID NO 41
<211> LENGTH: 17
<212> TYPE: DNA
<213> ORGANISM: Artificial Sequence
<220> FEATURE:
<223> OTHER INFORMATION: Chemically Synthesized Primer

<400> SEQUENCE: 41
agtggggttt ggagact                                                   17

<210> SEQ ID NO 42
<211> LENGTH: 16
<212> TYPE: DNA
<213> ORGANISM: Artificial Sequence
<220> FEATURE:
<223> OTHER INFORMATION: Chemically Synthesized Primer

<400> SEQUENCE: 42
ctggttaggg aaacaa                                                    16

<210> SEQ ID NO 43
<211> LENGTH: 18
<212> TYPE: DNA
<213> ORGANISM: Artificial Sequence
<220> FEATURE:
<223> OTHER INFORMATION: Chemically Synthesized Primer

<400> SEQUENCE: 43
cttccctctt tctgtgag                                                  18

<210> SEQ ID NO 44
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 44
gtcttttaaa tttgtagttc                                                20

<210> SEQ ID NO 45
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 45
atttgctcag tcaaaatatg                                                20

<210> SEQ ID NO 46
<211> LENGTH: 15
<212> TYPE: DNA
<213> ORGANISM: Artificial Sequence
<220> FEATURE:
<223> OTHER INFORMATION: Chemically Synthesized Primer

<400> SEQUENCE: 46
ggcagccaag gggag                                                     15

<210> SEQ ID NO 47
<211> LENGTH: 19
<212> TYPE: DNA
<213> ORGANISM: Artificial Sequence
<220> FEATURE:
<223> OTHER INFORMATION: Chemically Synthesized Primer
```

```
<400> SEQUENCE: 47
tgccctctac taatgtcac                                                  19

<210> SEQ ID NO 48
<211> LENGTH: 19
<212> TYPE: DNA
<213> ORGANISM: Artificial Sequence
<220> FEATURE:
<223> OTHER INFORMATION: Chemically Synthesized Primer

<400> SEQUENCE: 48
gctgtggata tacccctta                                                  19

<210> SEQ ID NO 49
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t

<400> SEQUENCE: 49
tattacatat attaataaga agtcangtaa cgagatgttt taagttctga a              51

<210> SEQ ID NO 50
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or t
<220> FEATURE:
<221> NAME/KEY: misc_feature
<222> LOCATION: (26)..(26)
<223> OTHER INFORMATION: n is a, c, g, or t

<400> SEQUENCE: 50
atcagtttat aggtcaaata tctacngcaa actcttcacc gctgtaactt a              51

<210> SEQ ID NO 51
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or g
<220> FEATURE:
<221> NAME/KEY: misc_feature
<222> LOCATION: (26)..(26)
<223> OTHER INFORMATION: n is a, c, g, or t

<400> SEQUENCE: 51
tagattaggt attttaaaaa ctggtncatt tttaagttgc tttaagtaag t              51

<210> SEQ ID NO 52
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or g
<220> FEATURE:
<221> NAME/KEY: misc_feature
<222> LOCATION: (26)..(26)
<223> OTHER INFORMATION: n is a, c, g, or t
```

<400> SEQUENCE: 52
aattggcagt gaaaaattat agatangcaa aaagctcctt ctgaggtcca g          51

<210> SEQ ID NO 53
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or c
<220> FEATURE:
<221> NAME/KEY: misc_feature
<222> LOCATION: (26)..(26)
<223> OTHER INFORMATION: n is a, c, g, or t

<400> SEQUENCE: 53
agaatatgca ctgttgtaaa gcctgngtat tttacttggc agctattttc a          51

<210> SEQ ID NO 54
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t

<400> SEQUENCE: 54
tgtggagtat gtgttggagg tgagtngcta gctgaagaat taaaacaata g          51

<210> SEQ ID NO 55
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or c
<220> FEATURE:
<221> NAME/KEY: misc_feature
<222> LOCATION: (26)..(26)
<223> OTHER INFORMATION: n is a, c, g, or t

<400> SEQUENCE: 55
cttacaattc aagggcattt agaacncttt gtcatctgtt aatattcaga a          51

<210> SEQ ID NO 56
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or g
<220> FEATURE:
<221> NAME/KEY: misc_feature
<222> LOCATION: (26)..(26)
<223> OTHER INFORMATION: n is a, c, g, or t

<400> SEQUENCE: 56
attctgacac gctcaggtac ctcaangaat cctccaactt cccaccttca c          51

<210> SEQ ID NO 57
<211> LENGTH: 51
<212> TYPE: DNA
<213> ORGANISM: Homo sapiens
<220> FEATURE:

```
<221> NAME/KEY: misc_feature
<223> OTHER INFORMATION: single nucleotide polymorphism; n can be c or t
<220> FEATURE:
<221> NAME/KEY: misc_feature
<222> LOCATION: (26)..(26)
<223> OTHER INFORMATION: n is a, c, g, or t

<400> SEQUENCE: 57
taatggccag caatttagta ttgccngact tttactaatg catgtgctgt t         51

<210> SEQ ID NO 58
<211> LENGTH: 51
<212> TYPE: DNA
<213> ORGANISM: Homo sapiens
<220> FEATURE:
<221> NAME/KEY: misc_feature
<223> OTHER INFORMATION: single nucleotide polymorphism; n can be a or g
<220> FEATURE:
<221> NAME/KEY: misc_feature
<222> LOCATION: (26)..(26)
<223> OTHER INFORMATION: n is a, c, g, or t

<400> SEQUENCE: 58
ttgtatttaa tctataccag caaganggca cttaatattg caagctttta a          51

<210> SEQ ID NO 59
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 59
catatattaa taagaagtca                                             20

<210> SEQ ID NO 60
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 60
cagtttatag gtcaaatatc                                             20

<210> SEQ ID NO 61
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 61
cttaaagcaa cttaaaaatg                                             20

<210> SEQ ID NO 62
<211> LENGTH: 18
<212> TYPE: DNA
<213> ORGANISM: Artificial Sequence
<220> FEATURE:
<223> OTHER INFORMATION: Chemically Synthesized Primer

<400> SEQUENCE: 62
tcagaaggag cttttttgc                                              18

<210> SEQ ID NO 63
<211> LENGTH: 19
```

```
<212> TYPE: DNA
<213> ORGANISM: Artificial Sequence
<220> FEATURE:
<223> OTHER INFORMATION: Chemically Synthesized Primer

<400> SEQUENCE: 63
aatagctgcc aagtaaaat                                                   19

<210> SEQ ID NO 64
<211> LENGTH: 18
<212> TYPE: DNA
<213> ORGANISM: Artificial Sequence
<220> FEATURE:
<223> OTHER INFORMATION: Chemically Synthesized Primer

<400> SEQUENCE: 64
gtatgtgttg gaggtgag                                                    18

<210> SEQ ID NO 65
<211> LENGTH: 18
<212> TYPE: DNA
<213> ORGANISM: Artificial Sequence
<220> FEATURE:
<223> OTHER INFORMATION: Chemically Synthesized Primer

<400> SEQUENCE: 65
ttcaagggca tttagaac                                                    18

<210> SEQ ID NO 66
<211> LENGTH: 15
<212> TYPE: DNA
<213> ORGANISM: Artificial Sequence
<220> FEATURE:
<223> OTHER INFORMATION: Chemically Synthesized Primer

<400> SEQUENCE: 66
gaagttggag gattc                                                       15

<210> SEQ ID NO 67
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 67
gccagcaatt tagtattgcc                                                  20

<210> SEQ ID NO 68
<211> LENGTH: 19
<212> TYPE: DNA
<213> ORGANISM: Artificial Sequence
<220> FEATURE:
<223> OTHER INFORMATION: Chemically Synthesized Primer

<400> SEQUENCE: 68
gcttgcaata ttaagtgcc                                                   19
```